(12) United States Patent
Bhatia et al.

(10) Patent No.: US 11,028,425 B2
(45) Date of Patent: Jun. 8, 2021

(54) DIAGNOSIS AND MONITORING OF LIVER DISEASE

(71) Applicant: GLYMPSE BIO, INC., Cambridge, MA (US)

(72) Inventors: Sangeeta Bhatia, Lexington, MA (US); Gabriel Kwong, Atlanta, GA (US); Eric Huang, Lexington, MA (US); Sirshendu Roopom Banerjee, Lexington, MA (US); Andrew Warren, Cambridge, MA (US); Sophie Cazanave, Cambridge, MA (US)

(73) Assignee: GLYMPSE BIO, INC., Cambridge, MA (US)

( * ) Notice: Subject to any disclaimer, the term of this patent is extended or adjusted under 35 U.S.C. 154(b) by 0 days.

(21) Appl. No.: 16/355,225

(22) Filed: Mar. 15, 2019

(65) Prior Publication Data
US 2019/0376114 A1 Dec. 12, 2019

Related U.S. Application Data

(60) Provisional application No. 62/682,505, filed on Jun. 8, 2018.

(51) Int. Cl.
*C12Q 1/37* (2006.01)

(52) U.S. Cl.
CPC ......... *C12Q 1/37* (2013.01); *G01N 2800/085* (2013.01); *G01N 2800/52* (2013.01)

(58) Field of Classification Search
CPC ............................................... G01N 2800/085
See application file for complete search history.

(56) References Cited

U.S. PATENT DOCUMENTS

| | | |
|---|---|---|
| 6,592,847 B1 | 7/2003 | Weissleder et al. |
| 7,179,655 B2 | 2/2007 | Patricelli |
| 7,329,506 B2 | 2/2008 | Ward et al. |
| 7,833,728 B2 | 11/2010 | Pastorek et al. |
| 8,551,727 B2 | 10/2013 | Kwon et al. |
| 8,673,267 B2 | 3/2014 | Bhatia et al. |
| 10,006,916 B2 | 6/2018 | Kwong et al. |
| 2004/0091943 A1 | 5/2004 | Schneider |
| 2010/0131432 A1 | 5/2010 | Kennedy et al. |
| 2010/0240050 A1 | 9/2010 | Bhatia et al. |
| 2013/0017223 A1 | 1/2013 | Hope et al. |
| 2013/0116405 A1 | 5/2013 | Yu et al. |
| 2015/0018517 A1 | 1/2015 | Rajopadhye et al. |
| 2015/0065420 A1 | 3/2015 | Soliman et al. |
| 2015/0132230 A1 | 5/2015 | Bossmann et al. |
| 2016/0206726 A1 | 7/2016 | Cobbold et al. |
| 2017/0049904 A1 | 2/2017 | Lin et al. |
| 2017/0176458 A1 | 6/2017 | Veidal et al. |
| 2017/0369843 A1 | 12/2017 | Kahvejian et al. |
| 2018/0023114 A1 | 1/2018 | Morin et al. |
| 2018/0085466 A1 | 3/2018 | Bradley et al. |
| 2018/0335429 A1 | 11/2018 | Bhatia et al. |

FOREIGN PATENT DOCUMENTS

| | | |
|---|---|---|
| WO | 0214867 A2 | 2/2002 |
| WO | 2004005348 A1 | 1/2004 |
| WO | 2008/127019 A1 | 10/2008 |
| WO | 2010/101628 A2 | 9/2010 |
| WO | 2012125808 A1 | 9/2012 |
| WO | 2014/079802 A2 | 5/2014 |
| WO | 2014/197816 A1 | 12/2014 |
| WO | 2014197840 A1 | 12/2014 |
| WO | 2017/177115 A1 | 10/2017 |
| WO | 2017/180587 A2 | 10/2017 |
| WO | 2017/193070 A1 | 11/2017 |
| WO | 2018/068135 A1 | 4/2018 |

OTHER PUBLICATIONS

Kwong et al., Nat Biotechnol., 2013, 31(1):63-70 cited in IDS and as printed/cited pp. 1-21.*
Dudani, 2016, Sustained-release synthetic biomarkers for monitoring thrombosis and inflammation using point-of-care compatible readouts, Adv Funct Mat 10.1002:1-10.
Kutlu, 2018, Molecular pathogenesis of nonalcoholic steatohepatitis (NASH) related hepatocellular carcinoma, Can J Gast Hepat 2018:8543763.
Kwong, 2013, Mass-encoded synthetic biomarkers for multiplexed urinary monitoring of disease, Nat Biotech 31 (1):63-70.
Kwong, 2015, Mathemetical framework for activity-based cancer biomarkers, PNAS 112(41):12627-12632.
Mallinckrodt, 2003, Assessing and interpreting treatment effects in longitudinal clinical trials with missing data, Biol Psychiatry 53:754-760.
Schuerle, 2016, Magnetically actuated protease sensors for in vivo tumor profiling, Nano Lett 16:6303-6310.
Warren, 2014, Disease detection by ultrasensitive quantification of microdosed synthetic urinary biomarkers, JACS 136:13709-13714.
Warren, 2014, Point-of-care diagnostics for noncommunicable diseases using synthetic urinary biomarkers and paper microfluidics, PNAS 111(10):3671-3676.

(Continued)

*Primary Examiner* — Bin Shen
(74) *Attorney, Agent, or Firm* — Brown Rudnick LLP; Thomas C. Meyers

(57) ABSTRACT

Methods and compositions for screening or diagnosis of liver disease are provided. The results may also indicate course and efficacy of treatment. The composition includes an activity sensor and a reporter releasably attached to the activity sensor. The method includes detecting the presence and/or amount of a reporter. The reporter is released from an activity sensor in the presence of diseased liver tissue but remains attached to the activity sensor in healthy tissue. The presence and/or amount of the reporter are used to characterize the liver disease. The liver disease may be nonalcoholic steatohepatitis (NASH) and results may further indicate staging of NASH.

9 Claims, 13 Drawing Sheets
Specification includes a Sequence Listing.

(56) References Cited

OTHER PUBLICATIONS

Aungier, 2016, The extracellular matrix: a new dimension in disease diagnosis and treatment, Biochem Soc 10-15.
Bonnans, 2014, Remodelling the extracellular matrix in development and disease, Nat Rev Mol cell Biol 15 (12):786-801.
Dudani, 2015, Photoactivated spatiotemporally responsive nanosensors of in vivo protease activity, ACS Nano 9 (12):11708-11717.
Dudani, 2018, Harnessing protease activity to improve cancer care, Ann Rev Cell Biol 2:353-76.
Friedman, 2013, The smart targeting of nanoparticles, Curr Pharm Des 19(35):6315-6329.
Gootenberg, 2017, Nucleic acid detection with CRISPR-Cas13a/C2c2, Science 356(6336):438-442.
Gootenberg, 2018, Multiplexed and portable nucleic acid detection platform with Cas13, Cas12a, and Csm6, Science 360(6387):439-444.
Gural, 2018, Engineered livers for infectious diseases, CMGH 5(2):131-143.
Hughes, 2017, Dissecting the role of the extracellular matrix in heart disease, Vet Sci 4(24):1-28.
International Search Report and Written Opinion dated Oct. 24, 2019, for PCT/US2019/036039, filed Jun. 7, 2019 (11 pages).
International Search Report and Written Opinion dated Sep. 12, 2019, for PCT/US2019/036036, filed Jun. 7, 2019 (9 pages).
International Search Report and Written Opinion dated Sep. 19, 2019, for PCT/US2019/036041, filed Jun. 7, 2019 (8 pages).
Kappelhoff, 2017, Overview of transcriptomic analysis of all human proteases, non-proteolytic homologs and inhibitors, BBA Mol Cell Res 1864:2210-2219.
Kircher, 2004, A dual fluorochrome probe for imaging proteases, Bioconjugate Chem 15:242-248.
Klingler, 2012, Profiling protease activities with dynamic proteomics workflows, Proteomics 12(4-5):587-596.
Kwon, 2017, Ultrasensitive tumor-penetrating nanosensors of protease activity, Nat Biomed Eng 1: art0054.
Lee, 2018, Implementation of a multiplex and quantitative proteomics platform for assessin protein lysates using DNA-barcoded antibodies, Mol Cell Proteomics 17(6):1245-1258.
Lin, 2013, Nanoparticles that sense thrombin activity as synthetic urinary biomarkers of thrombosis, ACS nano 7 (10):9001-9009.
Raagel, 2010, Peptide-mediate protein delivery—which pathways are penetrable?, Biochim et Biophys Acata 1798:2240-2248.
Tascilar, 1999, Role of tumor markers and mutations in cells and pancreatic juice in the diagnosis of pancreatic cancer, Ann Onc 10(Suppl 4):s107-s110.
Tockman, 1992, Consideratoins in bringing a cancer biomarker to clinical application, Canc Res 52:2711s-2718s.
Abudayyeh, 2012, Nanoparticle-chaperoned urinary "synthetic biomarkers" for profiling proteases in cancer, MIT Thesis.
Deshpande, 2013, Current trends in the use of liposomes for tumor targeting, Nanomed 8(9):1509-28.
Dudani, 2018, Classification of prostate cancer using a protease activity nanosensor library, PNAS 115(36):8954-8959.
Gang, 2018, Cyclic Peptides: Promising Scaffolds for Biopharmaceuticals, Genes 9:557.
Gural, 2018, Engineered livers for infection diseases, Cell Mol Gastroent Hepat 5(2):131-144.
Harris, 2008, Protease-triggered unveiling of bioactive nanoparticles, Small 4(9):1307-1312.
Holt, 2018, Nanosensors to cetect protease activity in vivo for noninvasive diagnostics, J Vis Exp 137:e57937.
International Search Report and Written Opinion dated Sep 4, 2019, for PCT/US19/36155, filed Jun 7, 2019 (8 pages).
Kristensen, 2016, Cell-penetrating peptides as tools to enhance non-injectable delivery of biopharmaceuticals, Tissue Barriers 4(2):e1178369.
Kwong, 2013, Mass-encoded synthetic biomarkers for multiplexed urinary monitorying of disease, Nat Biotech 31(1):63-70.
Lau, 2018, Therapeutic peptides: Historical perspectives, current development trends, and future directions, Bioorganic & Med Chem 26:2700-2707.
Lin, 2009, PEG Hydrogels for the controlled release of biomolecules in regenerative medicine, Pharma Res 26 (3):631-643.
Lin, 2013, The biodegradation of biodegradable polymeric biomaterials, Chapter II.4.3 in Biomaterials Science 3d Ed., Ratner et al., Eds Academic Press 716-728.
Lo, 2018, iRGD-guided tumor-penetrating nanocomplexes for therapeutic siRNA delivery to pancreatic cancer, Mol Cancer Ther 17(11):2377-2388.
Luther, 2018, Hepatic connexin 32 associates with nonalcoholic fatty liver disease severity, Hepatol Comm 2(7):786-797.
Milletti, 2012, Cell-penetrating peptides: classes, origin, and current landscape, Drug Disc Today 17:850-860.
Nguyen, 2011, The prototype HIV-1 maturation inhibitor, bevirimat, binds to the CA-SP1 cleavage site in immature Gag particles, Retrovirology 8:101 (13 pages).
Song, 2012, PROSPER: An integrated feature-based tool for predicting protease substrate cleavage sites, PLoSOne 7 (11):e50300 (23 pages).
Van Lehn, 2011, Penetration of lipid bilayers by nanoparticles with environmentally-responsive surfaces, Soft Matter 7:11392-11404.

\* cited by examiner

FIG. 5 *PRIOR ART

SEQUENCE LISTING

```
<160> NUMBER OF SEQ ID NOS: 75

<210> SEQ ID NO 1
<211> LENGTH: 8
<212> TYPE: PRT
<213> ORGANISM: Homo sapiens

<400> SEQUENCE: 1

Ser Ser Thr Ser Ser Trp Tyr Ser
1               5

<210> SEQ ID NO 2
<211> LENGTH: 8
<212> TYPE: PRT
<213> ORGANISM: Homo sapiens

<400> SEQUENCE: 2

Pro Cys Ile Gln Ala Glu Ser Glu
1               5
```

```
<210> SEQ ID NO 3
<211> LENGTH: 8
<212> TYPE: PRT
<213> ORGANISM: Homo sapiens

<400> SEQUENCE: 3

Asp Asp Glu Glu Ile Glu Leu Ala
1               5

<210> SEQ ID NO 4
<211> LENGTH: 8
<212> TYPE: PRT
<213> ORGANISM: Homo sapiens

<400> SEQUENCE: 4

Val Leu Glu Gln Val Val Thr Ser
1               5

<210> SEQ ID NO 5
<211> LENGTH: 8
<212> TYPE: PRT
<213> ORGANISM: Homo sapiens

<400> SEQUENCE: 5

Gln Val Val Gln Val Val Leu Asp
1               5

<210> SEQ ID NO 6
<211> LENGTH: 8
<212> TYPE: PRT
<213> ORGANISM: Homo sapiens

<400> SEQUENCE: 6

Lys Ser Ile Gln Glu Ile Gln Glu
1               5

<210> SEQ ID NO 7
<211> LENGTH: 8
<212> TYPE: PRT
<213> ORGANISM: Homo sapiens

<400> SEQUENCE: 7

Lys Asp Phe Ala Ala Glu Val Val
1               5

<210> SEQ ID NO 8
<211> LENGTH: 8
<212> TYPE: PRT
<213> ORGANISM: Homo sapiens

<400> SEQUENCE: 8

Thr Ser Tyr Ala Gly Tyr Ile Glu
1               5

<210> SEQ ID NO 9
<211> LENGTH: 8
<212> TYPE: PRT
<213> ORGANISM: Homo sapiens

<400> SEQUENCE: 9

Leu Lys Val Ala Gly Gln Asp Gly
1               5
```

```
<210> SEQ ID NO 10
<211> LENGTH: 8
<212> TYPE: PRT
<213> ORGANISM: Homo sapiens

<400> SEQUENCE: 10

Phe Cys Leu His Gly Gly Leu Ser
1               5

<210> SEQ ID NO 11
<211> LENGTH: 8
<212> TYPE: PRT
<213> ORGANISM: Homo sapiens

<400> SEQUENCE: 11

Trp Met Asp Phe Gly Arg Arg Ser
1               5

<210> SEQ ID NO 12
<211> LENGTH: 8
<212> TYPE: PRT
<213> ORGANISM: Homo sapiens

<400> SEQUENCE: 12

Ser Ala Thr Ala Ala Val Asn Pro
1               5

<210> SEQ ID NO 13
<211> LENGTH: 8
<212> TYPE: PRT
<213> ORGANISM: Homo sapiens

<400> SEQUENCE: 13

Arg Glu Leu Gly Leu Gly Arg His
1               5

<210> SEQ ID NO 14
<211> LENGTH: 8
<212> TYPE: PRT
<213> ORGANISM: Homo sapiens

<400> SEQUENCE: 14

Asp Glu Gly Asp Ser Leu Asp Gly
1               5

<210> SEQ ID NO 15
<211> LENGTH: 8
<212> TYPE: PRT
<213> ORGANISM: Homo sapiens

<400> SEQUENCE: 15

Asp Glu Thr Asp Met Ala Lys Leu
1               5

<210> SEQ ID NO 16
<211> LENGTH: 8
<212> TYPE: PRT
<213> ORGANISM: Homo sapiens

<400> SEQUENCE: 16

Glu Glu Cys Asp Ala Ala Glu Gly
1               5

<210> SEQ ID NO 17
<211> LENGTH: 8
```

```
<212> TYPE: PRT
<213> ORGANISM: Homo sapiens

<400> SEQUENCE: 17

Ala Glu Val Asp Gly Asp Asp Asp
1               5

<210> SEQ ID NO 18
<211> LENGTH: 8
<212> TYPE: PRT
<213> ORGANISM: Homo sapiens

<400> SEQUENCE: 18

Asp Arg His Asp Gly Thr Ser Asn
1               5

<210> SEQ ID NO 19
<211> LENGTH: 8
<212> TYPE: PRT
<213> ORGANISM: Homo sapiens

<400> SEQUENCE: 19

Val Glu Val Asp Ala Pro Lys Ser
1               5

<210> SEQ ID NO 20
<211> LENGTH: 8
<212> TYPE: PRT
<213> ORGANISM: Homo sapiens

<400> SEQUENCE: 20

Asp Gln Thr Asp Gly Leu Gly Leu
1               5

<210> SEQ ID NO 21
<211> LENGTH: 8
<212> TYPE: PRT
<213> ORGANISM: Homo sapiens

<400> SEQUENCE: 21

Asp Ser Ile Asp Ser Phe Glu Thr
1               5

<210> SEQ ID NO 22
<211> LENGTH: 8
<212> TYPE: PRT
<213> ORGANISM: Homo sapiens

<400> SEQUENCE: 22

Asp Asp Val Asp Thr Lys Lys Gln
1               5

<210> SEQ ID NO 23
<211> LENGTH: 8
<212> TYPE: PRT
<213> ORGANISM: Homo sapiens

<400> SEQUENCE: 23

Val Glu Met Asp Ala Ala Pro Gly
1               5

<210> SEQ ID NO 24
<211> LENGTH: 8
<212> TYPE: PRT
<213> ORGANISM: Homo sapiens
```

-continued

```
<400> SEQUENCE: 24

Val Ser Trp Asp Ser Gly Gly Ser
1               5

<210> SEQ ID NO 25
<211> LENGTH: 8
<212> TYPE: PRT
<213> ORGANISM: Homo sapiens

<400> SEQUENCE: 25

Glu Glu Thr Asp Gly Ile Ala Tyr
1               5

<210> SEQ ID NO 26
<211> LENGTH: 8
<212> TYPE: PRT
<213> ORGANISM: Homo sapiens

<400> SEQUENCE: 26

Val Glu Thr Asp Lys Ala Thr Val
1               5

<210> SEQ ID NO 27
<211> LENGTH: 8
<212> TYPE: PRT
<213> ORGANISM: Homo sapiens

<400> SEQUENCE: 27

Gly Ser Ser Asp Pro Leu Ile Gln
1               5

<210> SEQ ID NO 28
<211> LENGTH: 8
<212> TYPE: PRT
<213> ORGANISM: Homo sapiens

<400> SEQUENCE: 28

Asp Asp Ala Asp Tyr Lys Pro Lys
1               5

<210> SEQ ID NO 29
<211> LENGTH: 8
<212> TYPE: PRT
<213> ORGANISM: Homo sapiens

<400> SEQUENCE: 29

His Ile Ser Ser Leu Ile Lys Leu
1               5

<210> SEQ ID NO 30
<211> LENGTH: 8
<212> TYPE: PRT
<213> ORGANISM: Homo sapiens

<400> SEQUENCE: 30

Asp Pro Asn Asn Leu Leu Asn Asp
1               5

<210> SEQ ID NO 31
<211> LENGTH: 8
<212> TYPE: PRT
<213> ORGANISM: Homo sapiens

<400> SEQUENCE: 31
```

Asp Leu Ser Asp Leu Thr Ala Ala
1               5

<210> SEQ ID NO 32
<211> LENGTH: 8
<212> TYPE: PRT
<213> ORGANISM: Homo sapiens

<400> SEQUENCE: 32

Phe Ser Ala Tyr Ile Lys Asn Ser
1               5

<210> SEQ ID NO 33
<211> LENGTH: 8
<212> TYPE: PRT
<213> ORGANISM: Homo sapiens

<400> SEQUENCE: 33

Glu Ala Leu Pro Leu Leu Val Arg
1               5

<210> SEQ ID NO 34
<211> LENGTH: 8
<212> TYPE: PRT
<213> ORGANISM: Homo sapiens

<400> SEQUENCE: 34

Gln Gln Gly Ala Ile Gly Ser Pro
1               5

<210> SEQ ID NO 35
<211> LENGTH: 8
<212> TYPE: PRT
<213> ORGANISM: Homo sapiens

<400> SEQUENCE: 35

Gly Pro Pro Gly Ile Val Ile Gly
1               5

<210> SEQ ID NO 36
<211> LENGTH: 8
<212> TYPE: PRT
<213> ORGANISM: Homo sapiens

<400> SEQUENCE: 36

Met Asp Ile Ala Ile His His Pro
1               5

<210> SEQ ID NO 37
<211> LENGTH: 8
<212> TYPE: PRT
<213> ORGANISM: Homo sapiens

<400> SEQUENCE: 37

Phe Phe Lys Asn Ile Val Thr Pro
1               5

<210> SEQ ID NO 38
<211> LENGTH: 8
<212> TYPE: PRT
<213> ORGANISM: Homo sapiens

<400> SEQUENCE: 38

Gly Pro Leu Gly Ala Arg Gly Ile

```
1               5

<210> SEQ ID NO 39
<211> LENGTH: 8
<212> TYPE: PRT
<213> ORGANISM: Homo sapiens

<400> SEQUENCE: 39

His Leu Gly Gly Ala Lys Gln Val
1               5

<210> SEQ ID NO 40
<211> LENGTH: 8
<212> TYPE: PRT
<213> ORGANISM: Homo sapiens

<400> SEQUENCE: 40

Val Trp Ala Ala Glu Ala Ile Ser
1               5

<210> SEQ ID NO 41
<211> LENGTH: 8
<212> TYPE: PRT
<213> ORGANISM: Homo sapiens

<400> SEQUENCE: 41

Gly Pro Leu Gly Ala Arg Gly Ile
1               5

<210> SEQ ID NO 42
<211> LENGTH: 8
<212> TYPE: PRT
<213> ORGANISM: Homo sapiens

<400> SEQUENCE: 42

Glu Ser Gly Asp Tyr Lys Ala Thr
1               5

<210> SEQ ID NO 43
<211> LENGTH: 8
<212> TYPE: PRT
<213> ORGANISM: Homo sapiens

<400> SEQUENCE: 43

Val Ala Gln Asp Leu Asn Ala Pro
1               5

<210> SEQ ID NO 44
<211> LENGTH: 8
<212> TYPE: PRT
<213> ORGANISM: Homo sapiens

<400> SEQUENCE: 44

Ser Pro Asp Ala Leu Gln Asn Pro
1               5

<210> SEQ ID NO 45
<211> LENGTH: 8
<212> TYPE: PRT
<213> ORGANISM: Homo sapiens

<400> SEQUENCE: 45

Pro Pro Leu Lys Leu Met His Ser
1               5
```

<210> SEQ ID NO 46
<211> LENGTH: 8
<212> TYPE: PRT
<213> ORGANISM: Homo sapiens

<400> SEQUENCE: 46

Gly Pro His Leu Leu Val Glu Ala
1               5

<210> SEQ ID NO 47
<211> LENGTH: 8
<212> TYPE: PRT
<213> ORGANISM: Homo sapiens

<400> SEQUENCE: 47

Val Gly Pro Asn Leu His Gly Val
1               5

<210> SEQ ID NO 48
<211> LENGTH: 8
<212> TYPE: PRT
<213> ORGANISM: Homo sapiens

<400> SEQUENCE: 48

Gly Gly Gly Asn Lys Ile Gly Pro
1               5

<210> SEQ ID NO 49
<211> LENGTH: 8
<212> TYPE: PRT
<213> ORGANISM: Homo sapiens

<400> SEQUENCE: 49

Leu Ser Thr Ala Arg Phe Val Val
1               5

<210> SEQ ID NO 50
<211> LENGTH: 8
<212> TYPE: PRT
<213> ORGANISM: Homo sapiens

<400> SEQUENCE: 50

Val Thr Glu Asp Val Asp Ile Asn
1               5

<210> SEQ ID NO 51
<211> LENGTH: 8
<212> TYPE: PRT
<213> ORGANISM: Homo sapiens

<400> SEQUENCE: 51

Ser Ala Leu Ala Thr Thr Val Tyr
1               5

<210> SEQ ID NO 52
<211> LENGTH: 8
<212> TYPE: PRT
<213> ORGANISM: Homo sapiens

<400> SEQUENCE: 52

Gln Glu Leu Ile Ser Asn Ala Ser
1               5

<210> SEQ ID NO 53

```
<211> LENGTH: 8
<212> TYPE: PRT
<213> ORGANISM: Homo sapiens

<400> SEQUENCE: 53

Gln Glu Leu Ile Ser Asn Ala Ser
1               5

<210> SEQ ID NO 54
<211> LENGTH: 8
<212> TYPE: PRT
<213> ORGANISM: Homo sapiens

<400> SEQUENCE: 54

Trp Glu Leu Ile Ser Asn Ala Ser
1               5

<210> SEQ ID NO 55
<211> LENGTH: 8
<212> TYPE: PRT
<213> ORGANISM: Homo sapiens

<400> SEQUENCE: 55

Ser Gly Asn Tyr Ala Thr Val Ile
1               5

<210> SEQ ID NO 56
<211> LENGTH: 8
<212> TYPE: PRT
<213> ORGANISM: Homo sapiens

<400> SEQUENCE: 56

Ser Ile Gln Met Asn Val Ala Glu
1               5

<210> SEQ ID NO 57
<211> LENGTH: 8
<212> TYPE: PRT
<213> ORGANISM: Homo sapiens

<400> SEQUENCE: 57

Gln Gln Asn Tyr Gln Asn Ser Glu
1               5

<210> SEQ ID NO 58
<211> LENGTH: 8
<212> TYPE: PRT
<213> ORGANISM: Homo sapiens

<400> SEQUENCE: 58

Ser Ile Leu Arg Leu Ala Lys Ala
1               5

<210> SEQ ID NO 59
<211> LENGTH: 8
<212> TYPE: PRT
<213> ORGANISM: Homo sapiens

<400> SEQUENCE: 59

Lys Phe Gln Arg Ala Ile Thr Gly
1               5

<210> SEQ ID NO 60
<211> LENGTH: 8
<212> TYPE: PRT
```

```
<213> ORGANISM: Homo sapiens

<400> SEQUENCE: 60

Ala Glu Pro Lys Met His Lys Thr
1               5

<210> SEQ ID NO 61
<211> LENGTH: 8
<212> TYPE: PRT
<213> ORGANISM: Homo sapiens

<400> SEQUENCE: 61

Thr Ile Pro Arg Ala Ala Ile Asn
1               5

<210> SEQ ID NO 62
<211> LENGTH: 8
<212> TYPE: PRT
<213> ORGANISM: Homo sapiens

<400> SEQUENCE: 62

Ala Glu Phe Arg His Asp Ser Gly
1               5

<210> SEQ ID NO 63
<211> LENGTH: 8
<212> TYPE: PRT
<213> ORGANISM: Homo sapiens

<400> SEQUENCE: 63

Arg Arg Lys Arg Ile Val Gly Gly
1               5

<210> SEQ ID NO 64
<211> LENGTH: 8
<212> TYPE: PRT
<213> ORGANISM: Homo sapiens

<400> SEQUENCE: 64

Ala Met Ser Arg Met Ser Leu Ser
1               5

<210> SEQ ID NO 65
<211> LENGTH: 8
<212> TYPE: PRT
<213> ORGANISM: Homo sapiens

<400> SEQUENCE: 65

Pro Glu Pro Glu Gln Leu Lys Met
1               5

<210> SEQ ID NO 66
<211> LENGTH: 8
<212> TYPE: PRT
<213> ORGANISM: Homo sapiens

<400> SEQUENCE: 66

Gln Ser Lys Glu Ala Ile His Ser
1               5

<210> SEQ ID NO 67
<211> LENGTH: 8
<212> TYPE: PRT
<213> ORGANISM: Homo sapiens
```

<400> SEQUENCE: 67

Lys Leu Lys Glu Ala Ser Arg Ser
1               5

<210> SEQ ID NO 68
<211> LENGTH: 8
<212> TYPE: PRT
<213> ORGANISM: Homo sapiens

<400> SEQUENCE: 68

Arg Ala Lys Arg Ser Pro Lys His
1               5

<210> SEQ ID NO 69
<211> LENGTH: 8
<212> TYPE: PRT
<213> ORGANISM: Homo sapiens

<400> SEQUENCE: 69

Arg Lys Lys Arg Ser Thr Ser Ala
1               5

<210> SEQ ID NO 70
<211> LENGTH: 8
<212> TYPE: PRT
<213> ORGANISM: Homo sapiens

<400> SEQUENCE: 70

Ser Ala Met Ala Ala Asp Ser Asn
1               5

<210> SEQ ID NO 71
<211> LENGTH: 8
<212> TYPE: PRT
<213> ORGANISM: Homo sapiens

<400> SEQUENCE: 71

Thr Leu Leu Ala Asn Ile Asn Glu
1               5

<210> SEQ ID NO 72
<211> LENGTH: 8
<212> TYPE: PRT
<213> ORGANISM: Homo sapiens

<400> SEQUENCE: 72

Gln Ala Glu Glu Thr Tyr Glu Asn
1               5

<210> SEQ ID NO 73
<211> LENGTH: 8
<212> TYPE: PRT
<213> ORGANISM: Homo sapiens

<400> SEQUENCE: 73

Asp Val Ile Asp Met Ser Lys Glu
1               5

<210> SEQ ID NO 74
<211> LENGTH: 8
<212> TYPE: PRT
<213> ORGANISM: Homo sapiens

<400> SEQUENCE: 74

```
Glu Val Leu Ala Thr Pro Pro Ala
1               5

<210> SEQ ID NO 75
<211> LENGTH: 8
<212> TYPE: PRT
<213> ORGANISM: Homo sapiens

<400> SEQUENCE: 75

Ala Pro Val Pro Gly Thr Ala Trp
1               5
```

DIAGNOSIS AND MONITORING OF LIVER DISEASE

CROSS-REFERENCE TO RELATED APPLICATION

This application claims priority to U.S. Provisional Application Ser. No. 62/682,505, filed Jun. 8, 2018, the contents of which are incorporated by reference.

SEQUENCE LISTING

This application contains a sequence listing which has been submitted in ASCII format via EFS-Web and is hereby incorporated by reference. The ASCII-formatted sequence listing, created on Aug. 1, 2019, is named GLY-002-01US-Seqs_ST25.txt and is 10843 bytes in size.

TECHNICAL FIELD

The present disclosure relates generally to methods and compositions for monitoring physiological state of the liver, such as presence of disease or stage.

BACKGROUND

A large number of people suffer from liver diseases and conditions, including non-alcoholic fatty liver disease (NAFLD) and hepatocellular carcinoma (HCC). HCC is the most common type of primary liver cancer in adults and commonly occurs in people with liver disease. NAFLD is a condition in which excess fat accumulates in the liver of a person who drinks little or no alcohol. In NAFLD, more than 5-10% of the weight of the liver is fat tissue. NAFLD is the most common form of liver disease in children and has more than doubled over the past twenty years.

When a person suffers from excess fat in the liver, but also suffers from inflammation or swelling and liver cell damage, the resulting condition is known as non-alcoholic steatohepatitis (NASH). Over time, the inflammation and cell damage associated with NASH can lead to fibrosis, or scarring, of the liver. As more and more scar tissue forms, it becomes difficult for the liver to function. When there is long-term damage of the liver and severe and permanent scarring, the condition is known as cirrhosis. NASH is a progressive disease that may lead to liver failure, cancer, or liver transplant. For example, NASH cirrhosis is projected to be the most frequent reason for liver transplants in the United States by 2030. Therefore, accurate, early detection methods are needed, as NASH may be reversible with early detection.

SUMMARY

The present invention provides an accurate, noninvasive method for characterizing a physiological state of liver tissue by detecting activity of enzymes that are expressed in the liver differentially under the physiological state of interest. Compositions and methods of the disclosure are useful for detection and/or staging of liver diseases and disorders, such as is non-alcoholic fatty liver disease (NAFLD), non-alcoholic steatohepatitis (NASH), hepatocellular carcinoma (HCC), alcoholic liver disease, genetic liver diseases, autoimmune liver diseases, toxicity-induced liver disease, or metastatic liver cancer. In particular, compositions and methods of the disclosure may be used to diagnosis a liver disease and/or to stage fibrosis. The invention comprises the use of compositions comprising an activity sensor to which is attached one or more reporter(s) that is (are) released in the liver only in the presence of enzymes that are differentially expressed under a physiological condition of interest such as a positive disease diagnosis or a certain stage of fibrosis. Compositions of the invention may be presented to a patient by any acceptable means, including orally, intravenously, sublingually, transdermally, and others. The invention provides the ability to screen, diagnose, stage, predict outcome, and/or inform therapeutic choice with respect to disease in, or physiological condition of, the liver. The reporter elements are released from the core or carrier portion of the activity sensor upon encountering enzymes that are differentially expressed under a condition of the disease. In a preferred instance, release is accomplished through enzymatic activity, where enzymes that are present at a characteristic abundance (e.g., differentially over-expressed or under-expressed) in a disease (or at a particular stage of disease) catalyze the release of reporters that are then processed or trafficked into a body fluid, ideally urine via the kidneys. Compositions of the disclosure are useful for diagnosing a liver disease such as NASH, NAFLD, or HCC and also for staging a condition such as fibrosis and do so by reporting a particular physiological state of liver tissue, e.g., by reporting on enzyme(s) that are differentially expressed in the liver tissue under the particular physiological state.

As discussed below, it is known that the liver accumulates both endogenous and exogenously-administered materials. In most diagnostic assays, signal from the liver is ignored or is treated as background because it is thought that administered compounds accumulate in the liver and create "noise" that obscures or dilutes signal from other sources in the body. The invention makes use of the liver's ability to accumulate exogenous material and uses that property to advantage in producing a signal that is highly-specific and sensitive to a number of disease states.

The core of the activity sensor can be any molecule that is capable of accumulation in the liver and that avoids triggering a significant immune response. Some detectable but trivial immune response may be present upon administration, but is ideally below a predetermined threshold. The core must also be capable of carrying or housing reporters for release in the presence of disease. Preferred carrier molecules are discussed below and include proteins, lipids, nanoparticles, and combinations of any of those.

Reporters can be any molecule that is detectable in a body fluid sample, such as urine. In a one aspect, reporters such as peptide fragments are released under defined conditions, processed through the kidneys, and detected in urine. Ideally, reporters are peptides that have a target sequence for cleavage by a protease. The proteases present in many disease states in the liver are unique to a particular disease or disease state (or stage). The invention makes use of the association of proteases with disease state or stage as a means to cleave reporters, which then will be detected as unique markers for disease. While the reporter can be a peptide that can be sequenced or otherwise detected in urine, it is also contemplated that reports can be non-peptide labels that are attached to activity sensors via a linkage, which can be a peptide sequence that is a target of an enzyme. However, release of reporters from activity sensors can also be accomplished through other means, such as light activation, ultrasound, and other means. Reporters can also be multiplexed in any convenient manner in order to increase specificity and/or sensitivity. For example, one may wish to include reporters that are linked via peptide recognition sequences for a number of different proteases or that are recognized by multiple proteases. For example, sequences that are cleaved by MMP-9 and MMP-2 may be used in order to assess for the presence of either of those proteases in the case in which they are diagnostic of the same or a related condition. In addition, multiple reporters designed to assess different disease states can be used to multiplex the diagnostic/screen.

It is also contemplated that the amount of reporter detected and the rate at which the reporter is released is related to disease stage and is informative not only as to diagnosis, but also as to potential therapy. One way in which that is done is by using the invention to obtain information on fibrosis staging and rate of progression, which allows the present invention to be used as a screening along a continuum of liver health. For example, fibrosis staging represents the progression of fibrosis along the continuum, and is indicated by the labels F0, F1, F2, F3, and F4. Quantitative measurement of released reporters and the rate of released reporters are useful for staging fibrosis and can be used alone or as an adjunct to traditional diagnostics, such as imaging, biopsy, and ultrasound. The present invention is also useful to predict clinical efficacy of various therapeutic interventions. For example, the rate of fibrosis progression or regression as determined by methods of the invention is indicative of therapeutic efficacy.

In general, an activity sensor for use in the invention may be any carrier that is capable of being administered to a patient and that accumulates in the liver. A preferred activity sensor comprises an inert core, an optional linker, and a reporter. The core may be any suitable core, such as an inorganic molecule, an organic molecule, or a polymer. The core preferably is a polymer composition, such as a polyethylene glycol (PEG) composition, and the reporter may be derived from a peptide library that may be barcoded in any manner known in the art.

As a non-limiting example of protease promiscuity, MMP9 is an enzyme that may be active to cleave a first sequence in a designed substrate or reporter for an activity sensor. MMP2 may be active for cleaving a second sequence in a designed substrate. Because the enzymes are cross-react, MMP2 may cleave the first sequence even though it typically cleaves the second sequence. This means that the substrates designed for particular protease activity and cleavage in the activity sensors of the present invention may be the same because of enzyme promiscuity.

Preferred activity sensors include nanoparticles, inorganic molecules, and organic molecules. The activity sensor may act as a pharmacokinetic switch. For example, one can measure an amount of intact (i.e., un-cleaved) reporter and an amount of cleaved reporter to assess a signal relating to the presence or absence of disease, staging of disease, or the choice of or response to therapy. Generally, a switch is a material having two or more states and that may have different circulating activities (e.g., half-life) or dissociation constants.

In a preferred embodiment, activity sensors include polymers (such as PEG) or other vehicles for delivery to the liver. Polyethylene glycol is a preferred carrier (activity sensor), as it typically evades immune response, has a long serum half-life, and is easily accumulated in the liver. Activity sensors may be multiplexed for high specificity and differential diagnosis. Released reports are detected in any body fluid sample, but can also be detected in tissue samples obtained from the patient. A preferred mode of detection is in urine, as released reporter molecules are processed via the kidneys and extracted in urine. Other possible bodily fluids for detection include blood, sputum, saliva, and feces.

Reporters preferably are barcoded for easy detection and association with specific enzymes as detailed below. Barcoding can be sequence-based or can be synthetic markers indicative of a particular reporter or group of reporters cleaved by a protease or group of proteases. Reporters can be used to determine stage and rate of disease in a single assay. Additionally, reporters can be multiplexed for detection of multiple enzymes, which aids in the specificity and staging of NASH. Reporters may also be multiplexed for staging of a disease and rate of progression of a disease, such as a liver disease (e.g. NASH) or liver cancer (e.g. HCC).

The present invention also contemplates diagnostic methods. Such methods comprise administering a composition comprising an activity sensor with releasable reporter molecules to a subject. The composition may be administered by any suitable manner, e.g. by intravenous injection, by aerosol inhalation, by mouth, or by subcutaneous means. The activity sensor may be part of a timed-release mechanism and may contain targeting agents that promote accumulation in the liver. A sample may be collected after a specified time period, e.g. one hour after administration of the composition. The sample may be collected by any suitable means, e.g. by urine collection. The sample may then be analyzed, e.g. by mass spectrometry analysis, and the analysis may further use a disease classification algorithm. Results may be issued in the form of a clinical report that may or may not contain diagnostic or prescriptive information.

Compositions of the invention may include a plurality of carrier molecules, or activity sensors, each having a plurality of reports linked at a cleavage site. The reports are liberated from the activity sensor or carrier by protease cleavage. Detected reports can be used to produce a signature that is indicative of disease state and stage. One advantage of the invention is that the proteases active in NASH (which are indicative of the extent of fibrosis) can be readily determined. In one example, detection of at least about 10 proteases establishes a signature for NASH at fibrosis stage F2 or greater. RNA sequencing of a diseased sample liver may be used to identify proteases associated with the liver condition. As a non-limiting example, the proteases selected may be from the group consisting of FAP, MMP2, ADAMTS2, FURIN, MMP14, MMP8, MMP11, CTSD, CTSA, MMP12, MMP9, and ST14.

The carrier may be any suitable material, but preferably is a polyethylene glycol (PEG) polymer, such as 40 kDa eight-arm poly(ethylene glycol). Linking peptides to PEG allows for the peptides to withstand clearance by the kidneys within minutes of administration. Such linking with PEG creates a larger molecular structure and limits uptake to the cells. PEG is not immunogenic or toxic, thereby allowing for less frequent administration and lower doses.

Reporters may be made of any suitable material, and preferably are amino acids, peptides, or polypeptides. The cleavage site is designed to be cleaved by specified enzymes, or proteases, indicative of a disease. Although enzymatic cleavage is discussed herein, other methods may be used to cleave reporters. Cleavage by light, pH, ultrasound, and chemical cleavage are non-limiting examples of non-enzymatic activity cleavage.

In designing cleavable reporters, a unique platform was built to engineer nanosensors against protease-mediated diseases. In one embodiment, 566 proteases across 5 genetic families are identified as targets for activity sensors of the invention. The reporters are linked in a manner that allows specific cleavage by proteases identified to be involved with a disease to be detected. Because the reporters are engineered, the resulting readout may be by any suitable method. For example, the readout may be by mass spectroscopy, lateral flow, or ELISA.

In another feature of the invention, tissue may be used to identify proteases active with particular diseases or conditions, which then informs the design choice of the reporters. As an example, liver tissue is used to identify proteases active in liver disease. A liver sample from a patient with a known or suspected disease profile is obtained and RNA is sequenced in order to identify proteases expressed in the known or suspected disease state. Compositions of the invention are then designed so that protease cleavage sites are built into the reporters. A composition comprising the carrier and attached reporters is then administered to patients and the liberation of protease-specific reporters is determined. It is also contemplated that reporters are designed using algorithms based on proteases known to be involved in various disease states.

In certain aspects, the disclosure provides a method for characterizing liver disease. The method includes detecting a reporter that is released from an activity sensor differentially in diseased liver tissue versus healthy liver tissue and characterizing a liver disease based upon a presence and/or amount of said reporter. The reporter may be released in healthy liver tissue, but the activity sensor is designed for differential (e.g. greater) cleavage by enzymes that have been shown to be differentially expressed in liver tissue affected by the disease. The presence and/or amount may be determined in a urine sample obtained from a patient to whom the activity sensor was administered (e.g., by mass spectrometry). Methods of the disclosure may be used for determining a disease stage and/or for assessing a rate of progression or regression of a liver disease such as nonalcoholic steatohepatitis (NASH), non-alcoholic fatty liver disease (NAFLD), or hepatocellular carcinoma (HCC).

Methods and compositions of the disclosure may be used for determining a disease stage, and/or may be used for evaluating a physiological state of tissue or of a subject. For example, methods and compositions of the disclosure may be used to detect pregnancy, to detect tobacco use, to evaluate diet. In preferred embodiments, methods and compositions of the disclosure are used to detect, or determine a stage or, a liver disease. Methods may include detecting a plurality of reporters from a plurality of activity sensors, wherein different ones of the plurality of reporters are released by enzymes that are differentially active in the diseased liver tissue versus the healthy liver tissue. The enzymes differentially active in the diseased liver tissue may include a set of enzymes wherein activity of the set has been shown to correlate to a stage of the liver disease. The enzymes may include, for example, one or more of a serine protease, a cysteine protease, a threonine protease, an aspartic protease, or a metalloprotease Methods may include correlating quantities of the plurality of detected reporters to a rate of progression or regression of the liver disease. In some embodiments, the proteases are selected from the group consisting of FAP, MMP2, ADAMTS2, FURIN, MMP14, GZMB, PRSS8, MMP8, ADAM12, CTSS, CTSA, CTSZ, CASP1, ADAMTS12, CTSD, CTSW, MMP11, MMP12, GZMA, MMP23B, MMP7, ST14, MMP9, MMP15, ADAMDEC1, ADAMTS1, GZMK, KLK11, MMP19, PAPPA, CTSE, PCSK5, and PLAU. Preferred embodiments include determining a stage of NASH. The activity sensor may include a multi-arm polyethylene glycol (PEG) scaffold and the reporters comprise polypeptides linked to the PEG scaffold.

In related aspects, the disclosure provides compositions for screening or diagnosis of liver disease. A composition of the disclosure may include an activity sensor and a reporter releasably attached to the activity sensor. The reporter is released from the activity sensor in the liver in the presence of an enzyme that is differentially expressed in liver affected by a disease versus healthy liver. The reporter may be released from the activity sensor via enzymatic cleavage. Preferably, the composition includes a plurality of the activity sensors, wherein each activity sensors has a plurality of the reporters releasably attached thereto, wherein the plurality of activity sensors are released by a plurality of enzymes that are differentially expressed in liver affected by the disease. The plurality of enzymes may be FAP, MMP2, ADAMTS2, FURIN, MMP14, GZMB, PRSS8, MMP8, ADAM12, CTSS, CTSA, CTSZ, CASP1, ADAMTS12, CTSD, CTSW, MMP11, MMP12, GZMA, MMP23B, MMP7, ST14, MMP9, MMP15, ADAMDEC1, ADAMTS1, GZMK, KLK11, MMP19, PAPPA, CTSE, PCSK5, and PLAU (preferably, the composition includes detectable reporters specific to about eight to twenty or so of those enzymes). In some embodiments, the activity sensor comprises a molecular scaffold and the reporters comprise polypeptides linked to the scaffold. The molecular scaffold may include a polyethylene glycol (PEG) scaffold. The PEG scaffold may include a multi-arm PEG molecule of between about 30 and about 50 kDa.

In certain embodiments, the activity sensors are designed to query for a disease such as nonalcoholic steatohepatitis (NASH), non-alcoholic fatty liver disease (NAFLD), or hepatocellular carcinoma (HCC). The plurality of the reporters may each include a polypeptide (or a plurality of copies of the polypeptide) that includes a cleavage target of a protease that is differentially expressed in liver affected by the disease. Optionally, the plurality of reporters are selected to be cleaved by a set of enzymes that is differentially expressed in a liver affected by a certain stage of NASH. In preferred embodiments, when the composition is injected into a subject, the plurality of activity sensors collect in the liver. In an exemplary embodiment, when the plurality of activity sensors collect in a liver affected by NASH stage 2 or higher, the plurality of reporters are cleaved and released from the activity sensors. The cleaved reporters are detectable polypeptides that enter circulation, are filtered from circulation at the kidneys, and are excreted in urine. Optionally, for mass-spectrometry embodiments, the detectable polypeptides each has a mass-to-charge ratio that corresponds to an identity of a protease that cleaves that reporter.

DETAILED DESCRIPTION

NASH is a disease of protease dysregulation and results in fibrosis, inflammation, and cell death in the liver. NASH is a progressive disease that may lead to liver failure, cancer, liver transplant, and death. The most common liver cancer in adults, typically resulting from liver disease, is HCC. The conditions associated with NASH and HCC may be reversible with early detection. The present invention provides methods of detection and staging of liver diseases and conditions, such as NASH and HCC.

The present invention provides non-invasive diagnostic and screening methods. However, the present invention may be used in combination with other diagnostic and screening tests. For example, other diagnostic methods include, but are not limited to, liquid biopsy, tissue biopsy, elastography, biomarker serums, and imaging, such as ultrasound, magnetic resonance imaging (MRI), fluorescence imaging, and positron emission tomography (PET) or computed tomography (CT).

Optionally, the present invention may be used in combination or conjunction with imaging or biopsy. For example, longitudinal monitoring with the present invention and periodic testing with liquid biopsy or imaging techniques may be performed to assess disease progression and/or therapeutic selection or efficacy. Other suitable detection methods for liver conditions include, but are not limited to, liver biopsy, liquid biopsy, ultrasound imaging, elastography, and serum biomarkers, such as the OWLiver Test from Owl Metabolomics, 13C-methacetin breath test (MBT) from Exalenz Bioscience, Plasma Pro-C3 from Nordic Bioscience, Fibroscan from Echosens for transient elastography (TE) using ultrasound, Magnetic Resonance Elastography (MRE) by Resoundant, Inc., and LiverMultiScan from Perspectum Diagnostics.

Figure 1:
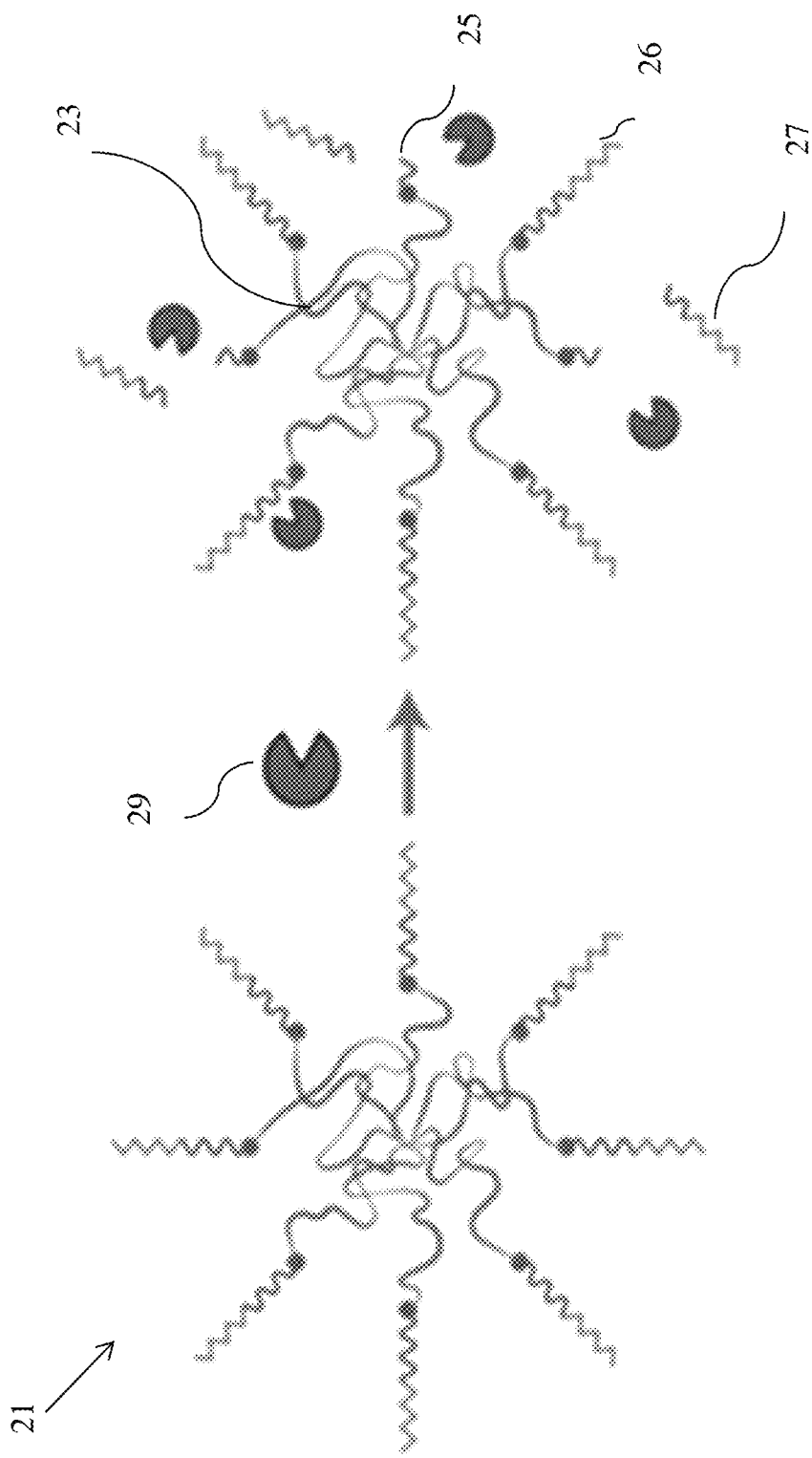
FIG. 1 illustrates an embodiment of an activity sensor of the present invention.

FIG. 1 illustrates an embodiment of an activity sensor of the present invention. The activity sensor 21 comprises a carrier or core 23 with reporter 26 attached thereto. When the carrier 21 is subjected to a protease 29, the protease 29 cleaves the reporter 26 at a cleavage site 25. The liberated reporter is then a detectable analyte 27. In a preferred embodiment, the carrier, or activity sensor, is a polyethylene glycol (PEG) polymer. For instance, the carrier may be PEG-MAL or PEG-840 kDa. PEG polymers are nontoxic and allow for accumulation in the liver. Use of the PEG carrier provides better bioavailability, circulation time, and safety. Although enzymatic cleavage is discussed herein, other methods may be used to cleave the reporters. Cleavage by light and chemical cleavage are non-limiting examples of cleavage that does not occur from enzymatic activity.

Figure 2:
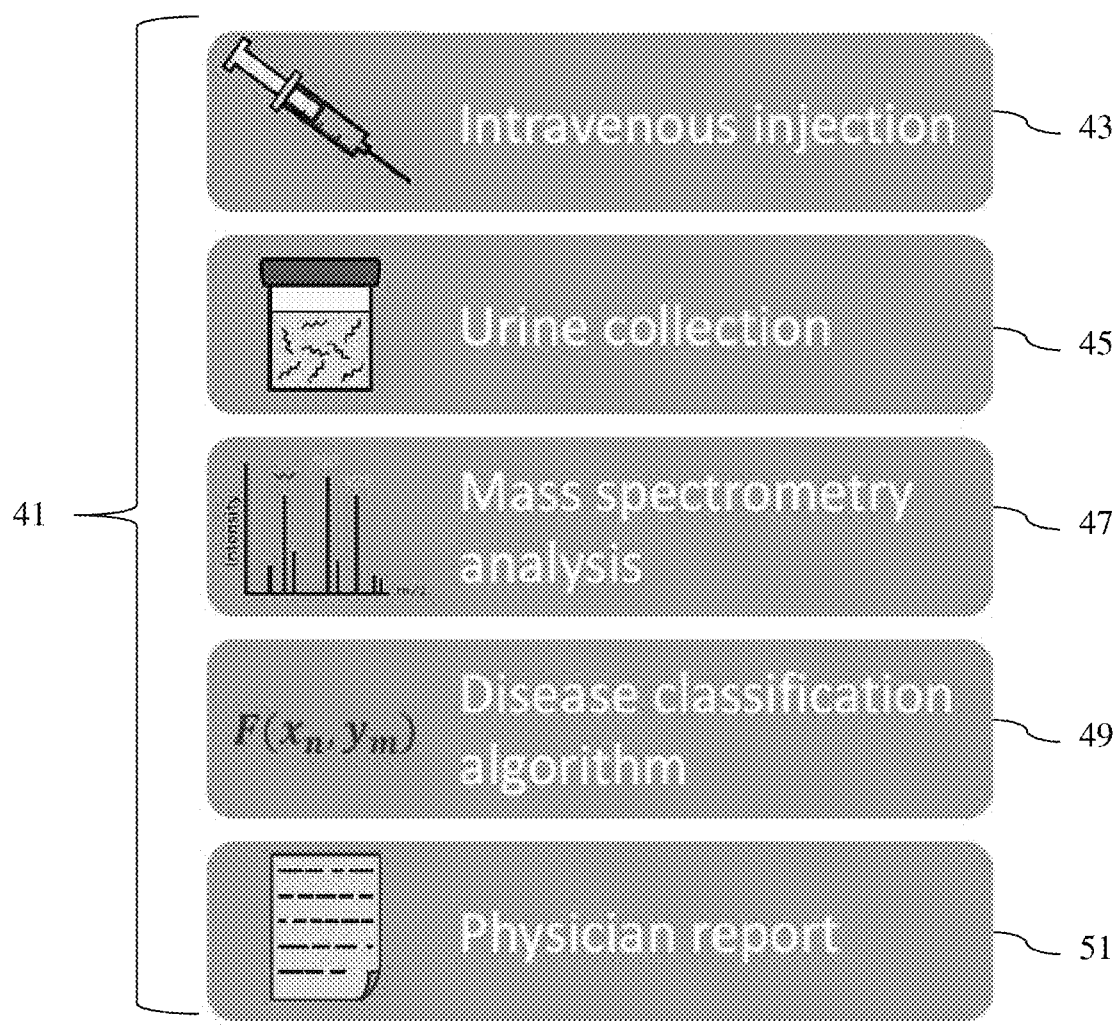
FIG. 2 illustrates a process of using the present invention.

FIG. 2 illustrates a method 41 of characterizing liver disease according to the disclosure. Compositions as described herein may be administered 43, for example by intravenous injection, to a subject. Where the composition includes the activity sensors 21, the activity sensors will collect in the liver. In the liver, the cleavage sites 25 are cleaved by proteases active in the liver. An insight of the disclosure is that the set of proteases active together in tissue at any given time provides a sensitive marker of disease and the stage of the disease. Also, because the activity sensors 21 provide an excess number of substrates for the enzymatic cleavage, the presence of detectable analyte 27 in a sample from the body may be measured quantitatively to give a measure of rate of activity of the proteases. Collectively, the rates of activity of the enzymes serve as an instantaneous measure of rate of progression of the disease. Accordingly, in the method 41, a sample, such as a urine sample, is collected 45. Because the activity sensors 21 are acted upon by the proteases present in the liver, the quantity of the detectable analytes 27 in the sample provides a measure of stage and rate of progression of disease. Thus, the sample is analyzed 47. Any suitable analysis may be used including, for example, an immune-assay using antibodies for the detectable analytes 27. In a preferred embodiment, the sample is analyzed 47 by mass spectrometry (which assays for a mass to charge ratio of polypeptides cleaved from the activity sensors 21). The output of the analysis 47 is provided to a classifier 49 that classifies a stage and/or rate of progression of disease in the tissue based on the output (e.g., peaks in a mass spectra). The classification 49 can be performed by a computer system that uses the classification results to provide 51 a report. The report describes a condition of the liver, such as a stage and/or rate of a progression of disease, and may be used by a physician to consult or treat a patient.

Activity sensors 21 of the disclosure include detectable reporters that are cleaved and released by enzymatic activity. In preferred embodiments, the reporters 26 of the activity sensors 21 are polypeptides that include cleavage sites of proteases and are cleaved by the proteases to release the detectable analytes 27. By including cleavage sites in the polypeptide reporters 26, the activity sensors 21 may be designed to report the activity of any proteases. Any suitable protease or protease category may be queried by the activity sensors 21, including, for example, cysteine proteases, aspartic proteases, serine proteases, threonine proteases, or metalloproteases.

Figure 3:
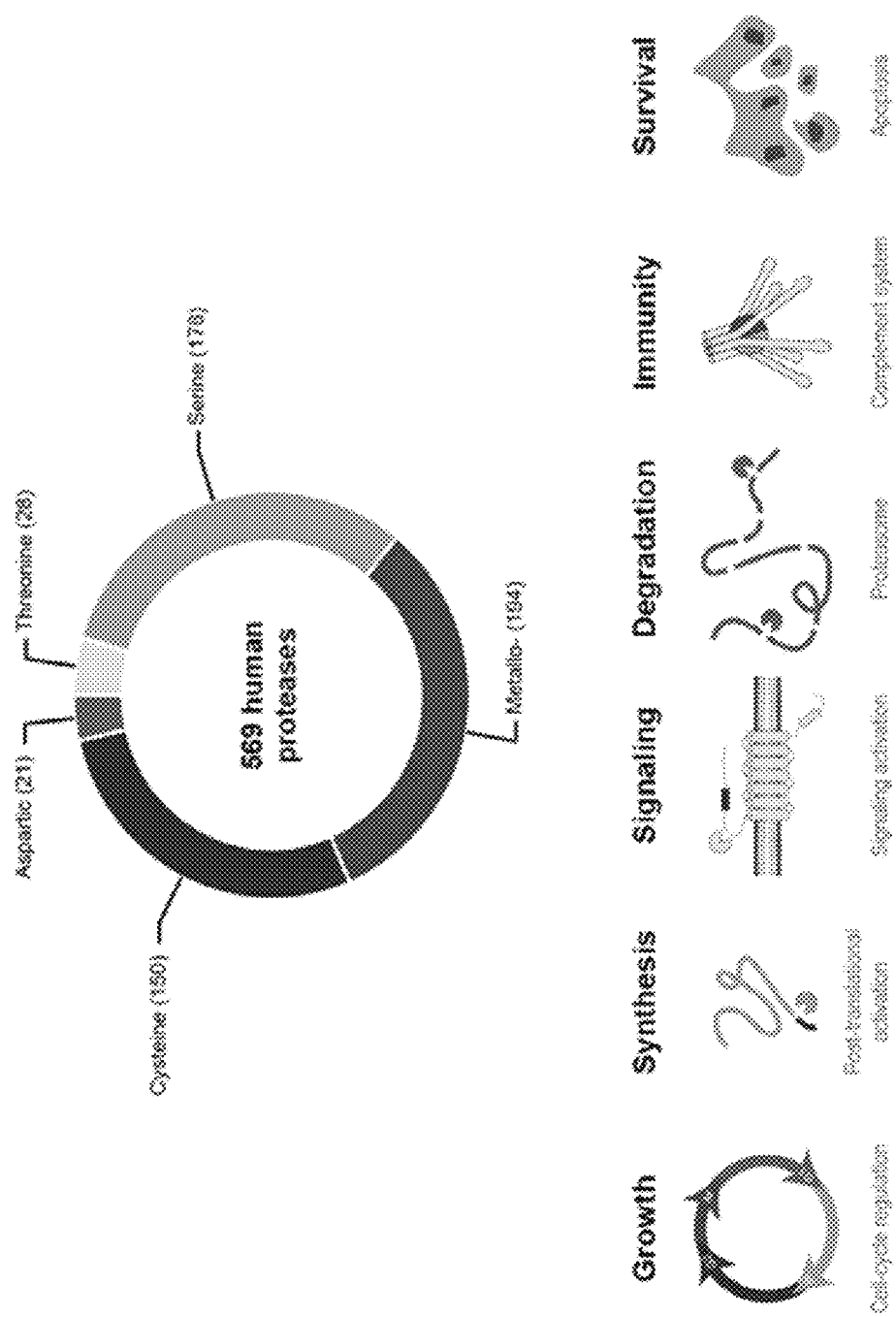
FIG. 3 shows categories of proteases.

FIG. 3 summarizes categories of proteases present in human cells across the 5 main enzymatic families. In particular, there are 569 human proteases, classified as metallo-, cysteine, aspartic, threonine, or serine proteases. Each of those is a target for activity sensors of the invention. The five main enzymatic families of proteases contribute to growth, synthesis, signaling, degradation, immunity, and survival in cells. Each of those families corresponds to respective catalytic mechanisms. Serine proteases have serine as the nucleophilic amino acid at the active site of the enzyme, cysteine proteases have a catalytic mechanism involving a nucleophilic cysteine thiol, and metalloproteases have catalytic mechanisms involving a metal. Similarly, catalytic mechanisms for aspartic proteases involve aspartate residue and catalytic mechanisms for threonine proteases involve threonine residue within the enzymatic active sites, respectively. In the present invention, dysregulated proteases that mediate key NASH pathways are used as targets for activity sensors of the invention. The dysregulated proteases include cathepsins, metalloproteases, trypsins, fibroblast activation protein (FAP), PLAU, CTSK, MMP-14, PRSS8, PLAT, CASP1, CTSD, ADAM28, GZMA, KLK11, MMP-2, -7, -9, -19, ADAMTS2, FAP, HTRA1, CTSZ, and others.

Figure 4:
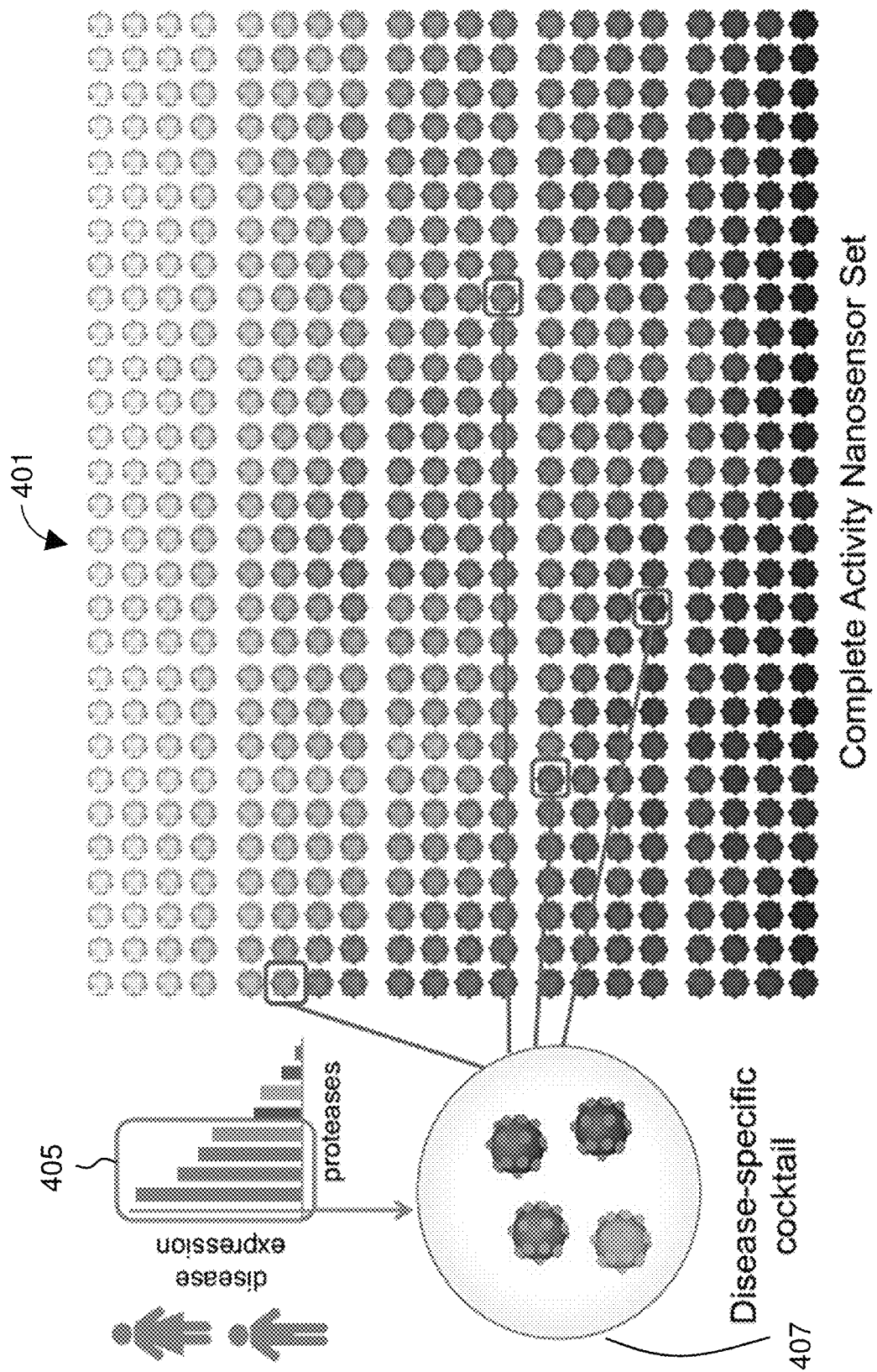
FIG. 4 shows the method for designing a disease-specific nanosensor cocktail.

FIG. 4 describes how proteases may be selected for inclusion in the activity sensors 21. A complete set 401, or library, of the activity nanosensors may be designed or made.

For a given liver disease or stage, patient samples may be used to create a profile 405 of a level of expression of each protease at the stage of disease. Based on those proteases that are expressed specifically in the disease condition, specific activity nanosensors 21 may be selected from the set 401 for inclusion in a composition 407 of the disclosure. The composition 407 preferably include one a plurality of activity sensors 21 that collectively include reporters 26 that are cleavable by those proteases found to be expressed specifically in the disease of interest and at a characteristic stage. A specific liver disease on the liver health continuum considered in the present invention is NASH. An insight of the disclosure is that NASH progresses by exploiting certain biological pathways that distinguish NASH from other liver injury such as cirrhosis. Those pathways involve the expression and activity of extracellular proteases that promote the progression of the disease. Moreover, the set of those proteases that are present and active at each stage of NASH will be characteristic to a specific stage and can distinguish NASH from other injury by the participation of those hallmark NASH pathways.

Figure 5:
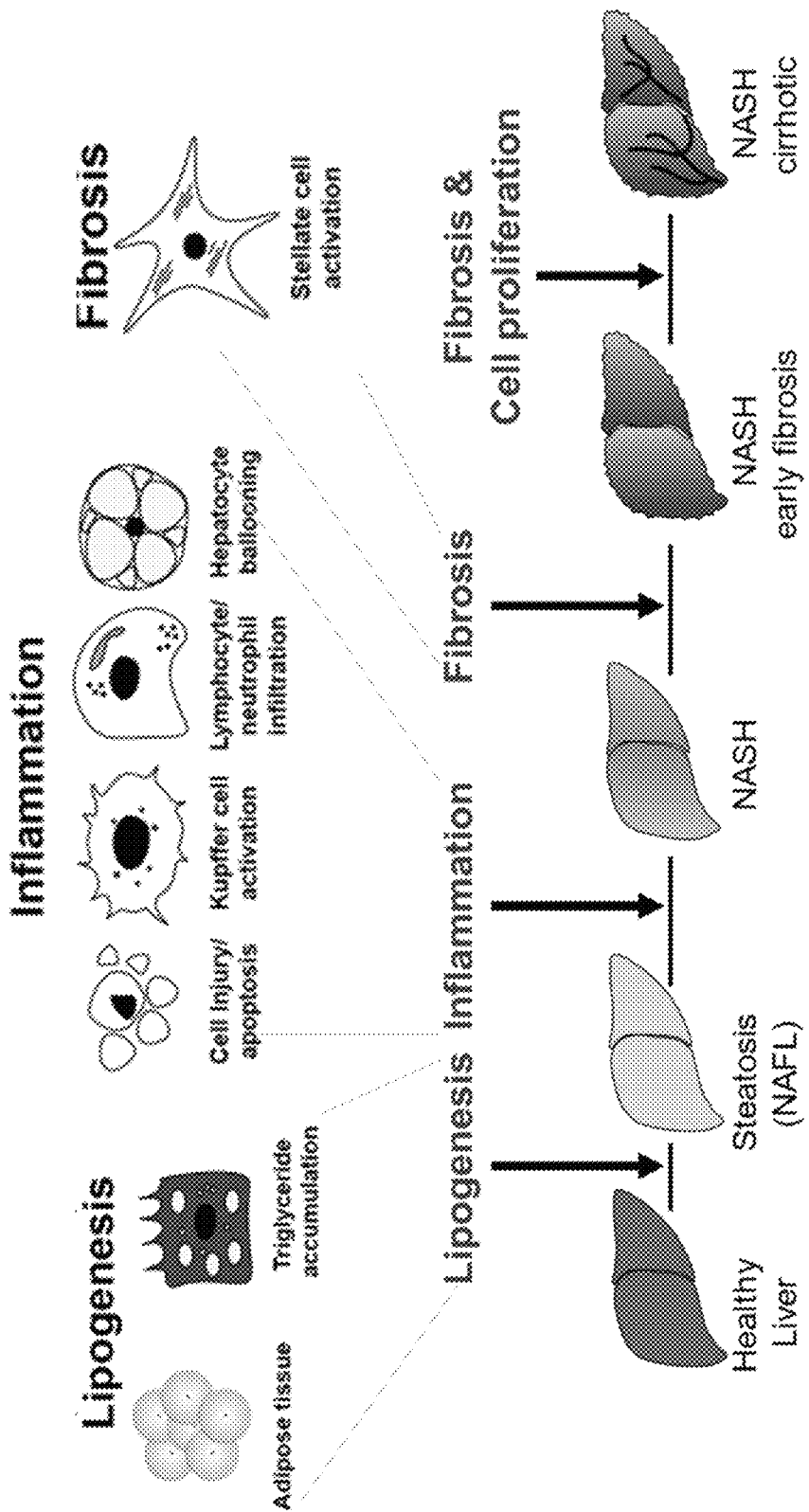
FIG. 5 shows biological pathways that distinguish NASH from other liver trauma.

FIG. 5 shows the four main pathways to NASH. As compared to other liver injury, NASH is characterized by distinct and specific protease activity in lipogenesis, inflammation, fibrosis, and proliferation pathways. The pathways are the indicators for NASH and differentiate NASH from other liver diseases such as cirrhosis or hepatic fibrogenesis. In NASH, the immune and inflammatory response involves an interaction among the liver, gut, and adipose tissue. Various factors, including metabolic factors and innate immune alterations, including inflammation cause by bacterial lipopolysaccharide (LPS), fatty acids, chemokines, cytokines, and adipokines, e.g. interleukin-6 (IL-6), tumor necrosis factor α (TNFα), contribute to inflammation in the liver and steatosis. The activity sensors provide the ability to diagnose multiple points along a pathway. In a preferred aspect of the invention, the pathway is the NASH liver health continuum, which is shown in FIG. 5.

Figure 6:
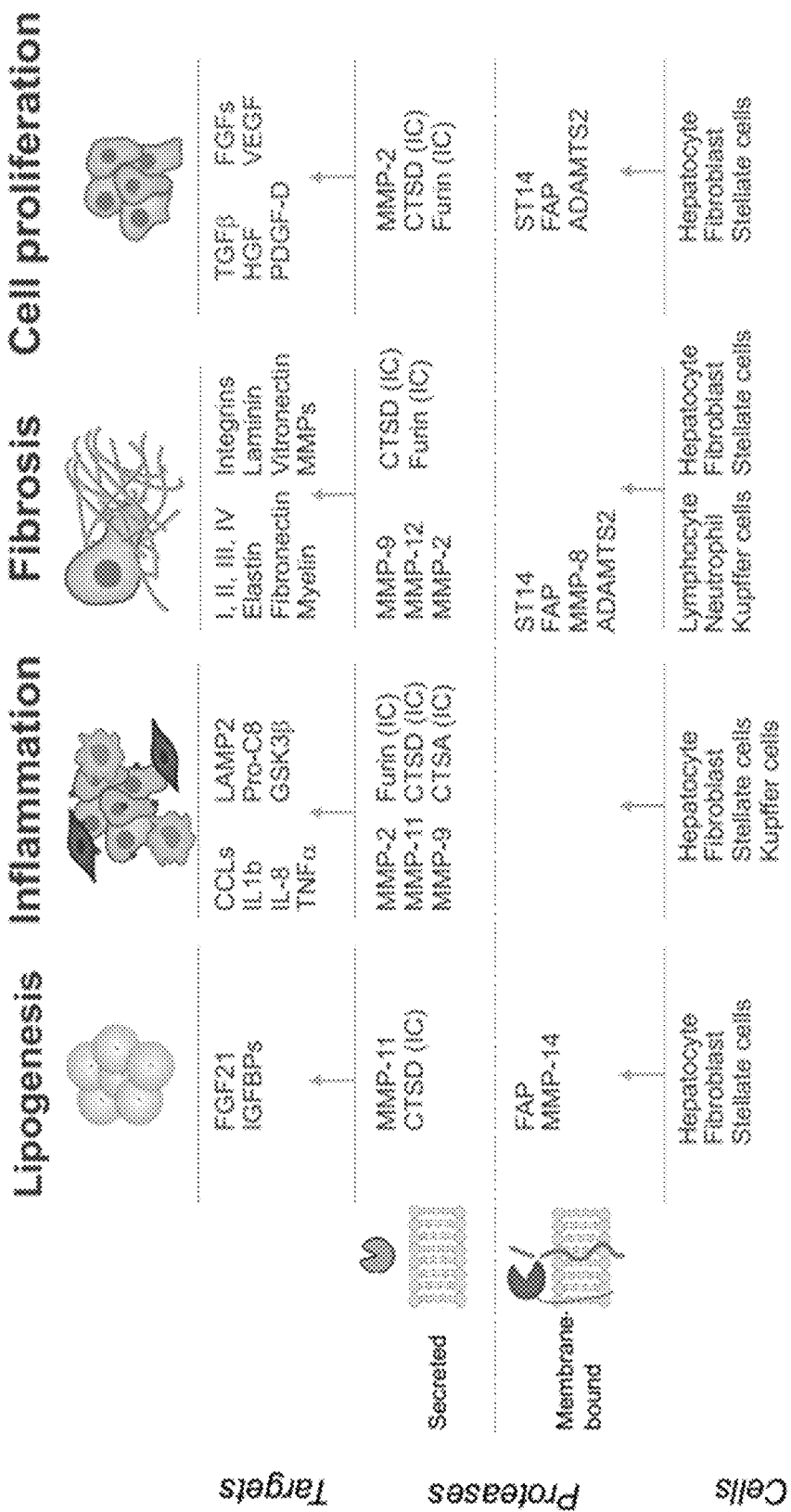
FIG. 6 shows participants in NASH pathways.

FIG. 6 shows the cells, secreted proteases, membrane-bound proteases, and targets that correspond to the pathways for lipogenesis, inflammation, fibrosis, and cell proliferation. For the lipogenesis pathway, FGF21 and IGFBPs are targets, MMP-11 and CTSD (IC) are secreted proteases, FAP and MMP-14 are membrane-bound proteases, and the cells are hepatocyte, fibroblast, and stellate cells. For example, in the inflammation pathway, CCLs, IL1b, IL-8, TNFα, LAMP2, Pro-C8, and GSK3β are targets, MMP-2, MMP-11, MMP-9, Furin (IC), CTSD (IC), and CTSA (IC) are secreted proteases, and the cells are hepatocyte, fibroblast, stellate cells, and Kupffer cells. For the fibrosis pathway, I, II, III, IV, Elastin, Fibronectin, Myelin, Integrins, Laminin, Virtonectin, and MMPs are targets, MMP-9, MMP-12, MMP-2, CTSD (IC), and Furin (IC) are secreted proteases, ST14, FAP, MMP-8, and ADAMTS2 are membrane-bound proteases, and the cells are lymphocyte, neutrophil, Kupffer cells, hepatocyte, fibroblast, and stellate cells. For the cell proliferation pathway, TGFβ, HGF, PDGF-D, FGFs, and VEGF are targets, MMP-2, CTSD (IC), and Furin (IC) are secreted proteases, ST14, FAP, and ADAMTS2 are membrane-bound proteases, and the cells are hepatocyte, fibroblast, and stellate cells.

Figure 7:
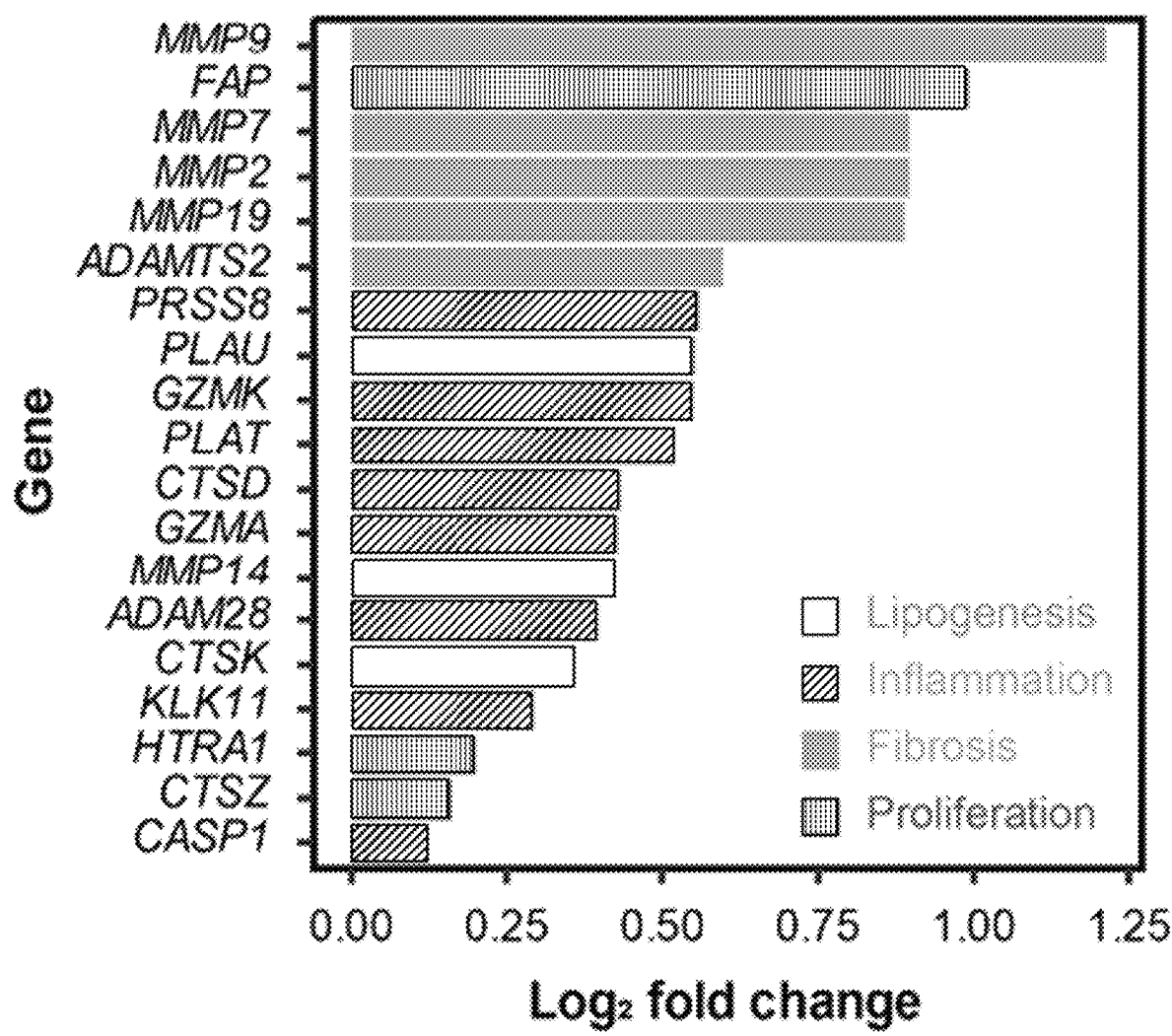
FIG. 7 gives the results of assaying for proteases that are active in NASH F2+.

FIG. 7 gives the results of assaying for proteases that are active in NASH at stage F2 and above differentially over NASH at stages 0 or 1 or other liver conditions. It is apparent from visual inspection that the proteases MMP9, MMP7, and MMP2, for example, are differentially highly expressed in NASH F2-F4 and are understood to be active in the fibrosis pathway. Similarly, the protease FAP is highly differentially expressed and is active in the proliferation pathway. Additionally, the protease PRSS8 is active in NASH F2 and contributes to the inflammation pathway. The protease PLAU is differentially expressed in NASH F2-F4 and contributes to the lipogenesis pathway. Thus it may be understood that constructing an activity sensor 21 with polypeptides as the reporters 26 and in which those polypeptides included the specific amino acid sequence that provide cleave sites for MMP9, FAP, MMP7, MMP2, MMP19, ADAMTS2, PRSS8, and PLAU, would provide a composition useful for non-invasively detecting activity in the liver in which hallmark proteases of all four biological pathways of NASH are probed to distinguish NASH from health or otherwise injured liver. Additionally, in this example, eight proteases are included. In some embodiments, the disclosure contemplates an 8-arm PEG scaffold as the carrier, with the reporters 26 linked to the PEG subunits. Using such a composition, the present disclosure is useful for diagnosis, staging, monitoring, and treatment of NASH at any stage, which may be a clinical trial entry criteria. As such, the present invention is used to identify NASH patients suitable for treatment.

Additionally, the measurement of the detectable reporters 27 in urine samples provides for very sensitive and specific detection of the stage and rate of progression of NASH.

Figure 8:
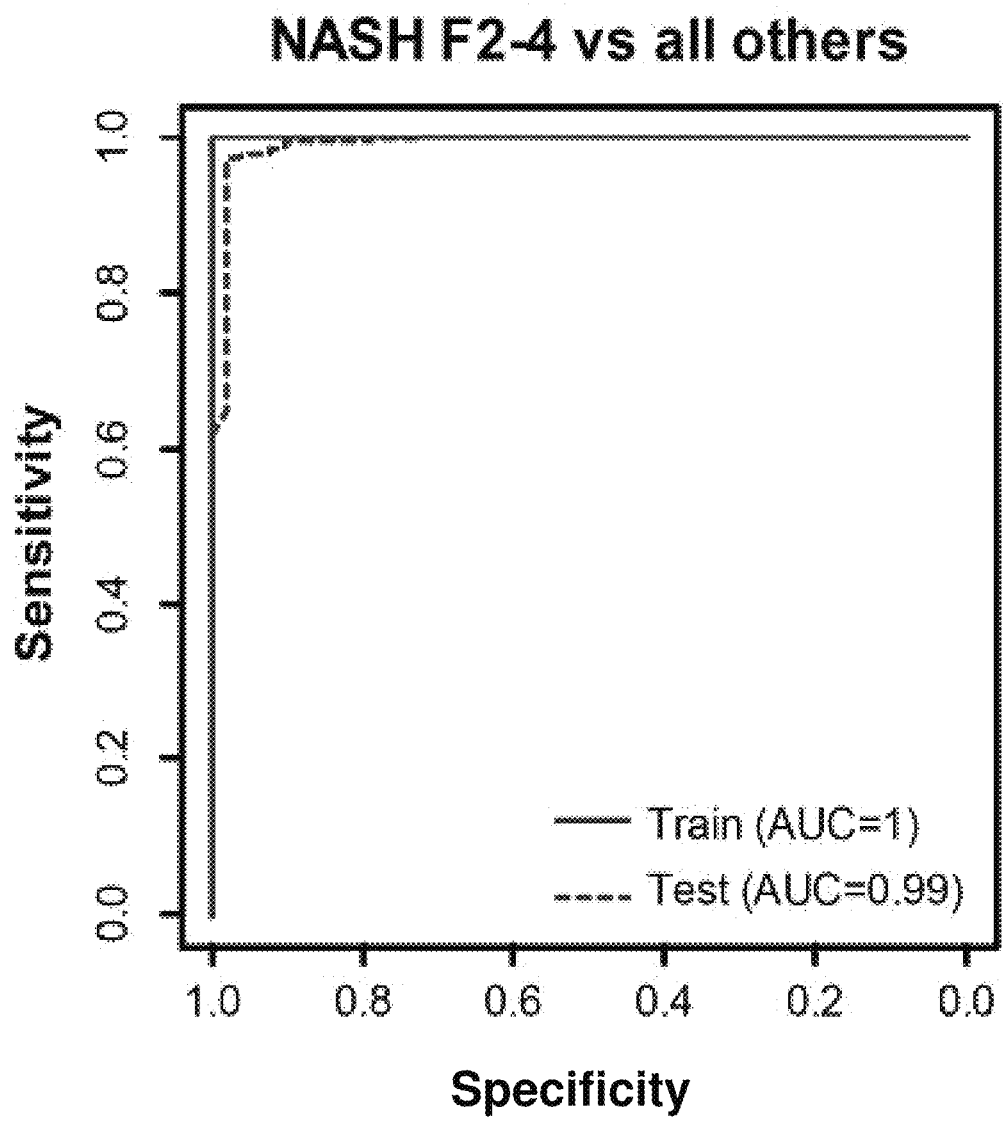
FIG. 8 shows the sensitivity and specificity in staging NASH F2+.

FIG. 8 shows the ROC for NASH F2-4 vs. a training set. The axes are sensitivity and specificity. The area under the curve (AUC) was 0.99.

Figure 9:
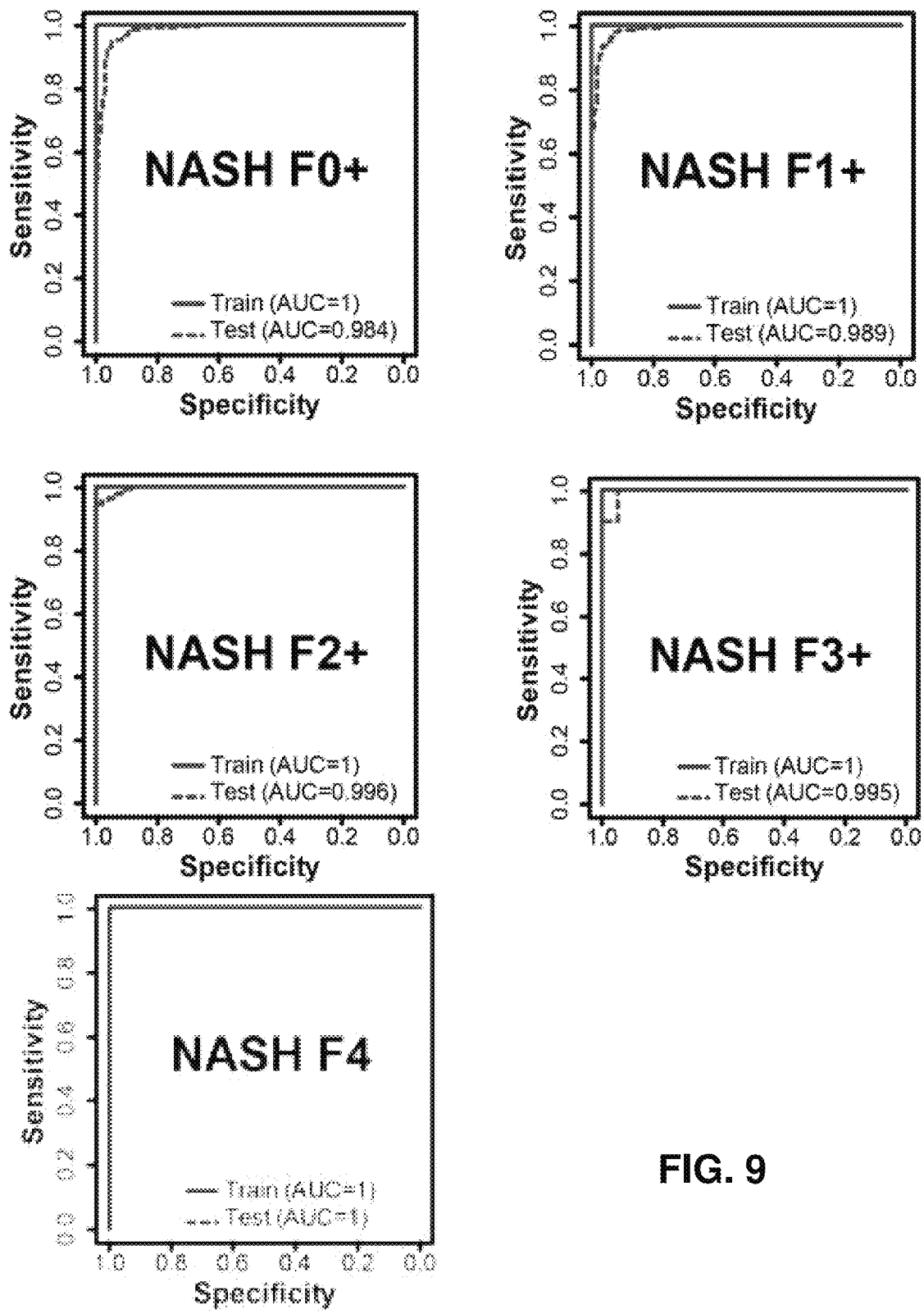
FIG. 9 shows detecting NASH at various stages.

FIG. 9 give the results from detecting NASH at each of a plurality of stages using compositions of the disclosure. In some embodiment, designing and providing the activity sensors 21 includes testing the activity sensors 21 in a subject and confirming the results by histology. By comparing the results of, e.g., multiple replicate trials with the activity sensors, the sensitivity or specificity of the activity sensors 21 may be empirically shown. The graphs show receiver-operator curves (ROC) for stages F0-F4. As shown, the AUC for F0+ was 0.984. For stage F1, the AUC was 0.989. For stage F2+, the AUC was 0.996. For stage F3+, the AUC was 0.995. For stage F4, the test AUC was 1.

Preferred embodiments of the disclosure include assaying for proteases that are differentially expressed in liver affected by NASH at a given stage, and methods my further include selecting a subset of those proteases to probe via the activity sensors 21. For example, by performing expression analysis (e.g., by RNA-Seq) on tissue samples from liver affected by a known stage of NASH, one may identify a large number e.g., tens, dozens, or more proteases that are active in the tissue. One may then select a limited number of those proteases for which it is sufficient to probe activity to stage NASH.

Figure 10:
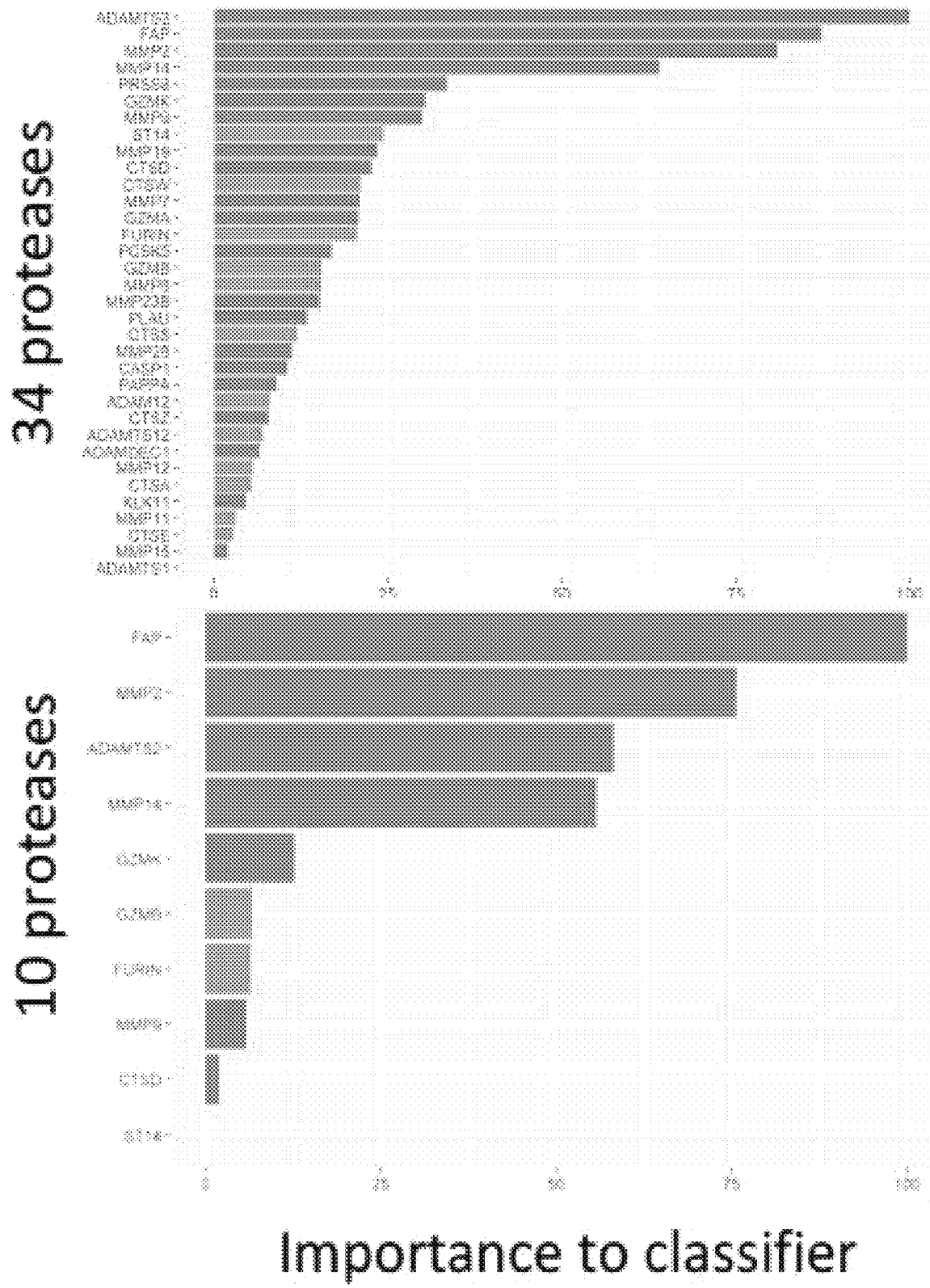
FIG. 10 illustrates selection of a subset of proteases.

FIG. 10 illustrate a set of 34 proteases that are identified as differentially expressed in NASH F2+ and then also a set of 10 of those proteases that are determined to be informative in classifying NASH stage. The 34 proteases include ADAMTS2, FAP, MMP2, MMP14, PRSS8, GZMK, MMP9, ST14, MMP19, CTSD, CTSW, MMP7, GZMA, FURIN, PCSK5, GZMB, MMP8, MMP23B, PLAU, CTSS, MMP28, CASP1, PAPPA, ADAM12, CTSZ, ADAMTS12, ADAMDEC1, MMP12, CTSA, KLK11, MMP11, CTSE, MMP15, and ADAMTS1. The initial 34 proteases are then narrowed to 10. Those included FAP, MMP2, ADAMTS2, MMP14, GZMK, GZMB, FURIN, MMP9, CTSD, and ST14. Tests may be performed to establish that the subset of a limited number of the differentially expressed proteases are useful to classify and stage NASH with statistical defensibility.

Figure 11:
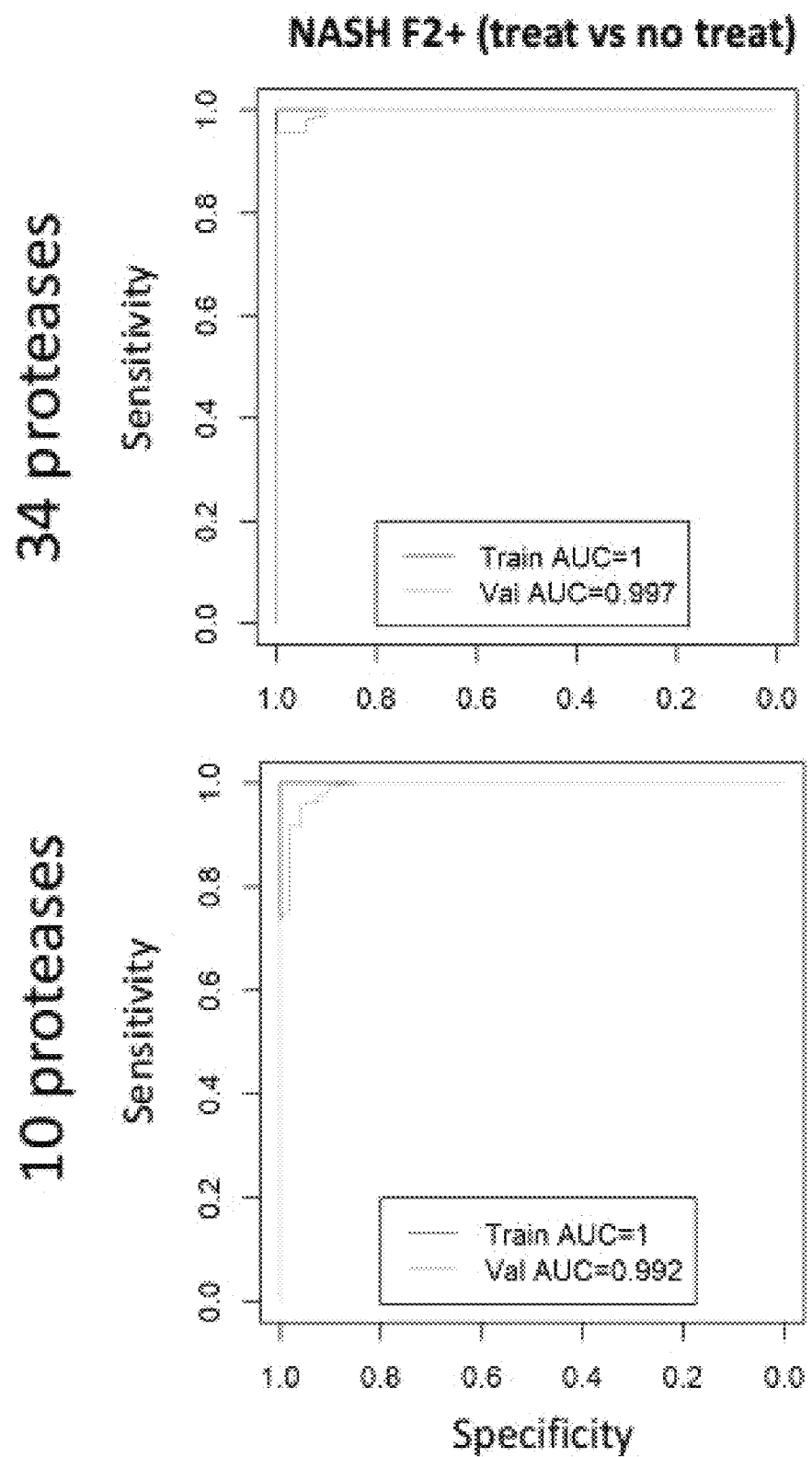
FIG. 11 shows the sensitivity of sets of proteases.

FIG. 11 shows the sensitivity of the full set of 34 proteases in classifying NASH stage and the sensitivity of the subset of 10 proteases for so classifying NASH. For the 34 ranked proteases, the validated AUC was 0.997. For the 10 ranked proteases, the validated AUC was 0.992. As such, it is clear that a high sensitivity and selectivity may be achieved using a subset of all of the proteases that are identified as differentially expressed in a stage of NASH.

Aspects of the invention provide a method for characterizing liver disease. The method includes detecting the presence of a reporter that is released from an activity sensor in the presence of diseased liver tissue but that remains attached to the activity sensor in healthy tissue and characterizing a liver disease based upon a presence and/or amount of said reporter. The presence and/or amount may be determined in a urine sample obtained from a patient to whom the activity sensor was administered. Preferably, the reporter is released via enzymatic cleavage, e.g., by a protease. The protease may include one or any of FAP, MMP2, ADAMTS2, FURIN, MMP14, MMP8, MMP11, CTSD, CTSA, MMP12, MMP9, and ST14. In certain embodiments, the liver disease is nonalcoholic steatohepatitis (NASH), non-alcoholic fatty liver disease (NAFLD), or hepatocellular carcinoma. Methods may be used for determining a stage of the disease, e.g., NASH.

In preferred embodiments, the activity sensor comprises a plurality of reporters. Each reporter may be associated with a presence of a protease in the liver. Preferably, the method includes establishing a NASH signature comprising at least about 10 proteases.

The activity sensor may include polyethylene glycol (PEG), e.g., a 40 kDa, multi-arm PEG scaffold to which the reporter polypeptides are linked.

Related aspects provide a composition for screening or diagnosis of liver disease. The composition includes an activity sensor with a reporter releasably attached to the activity sensor. The reporter is released from the activity sensor in the liver only in the presence of an enzyme associated with a liver condition such as nonalcoholic steatohepatitis (NASH). Preferably, the activity sensor includes a plurality (e.g., at least four, preferably about eight to about twelve) of reporters that are released by distinct enzymes via enzymatic cleavage in liver affected by the disease. Said enzymatic cleavage may be directed by a protease, with the reporters being polypeptides in which the activity sensor comprises a polyethylene glycol molecule.

Compositions and methods of the disclosure may be used to identify the stage of NASH, or the rate of progression. In preferred embodiments, methods include administering to a patient a composition comprising a plurality of the activity sensors 21 and measuring a quantity of the detectable analytes 27 in a sample from the patient such as a urine sample. The quantities of the several (preferably about four to about fourteen) distinct detectable reporters can show the stage of disease in the patient's liver, a rate of progression of the disease, or both. Additionally, methods and compositions of the disclosure may be used to profile a condition of a subject's liver to predict response to a therapy, to monitor treatment or remission, or to screen for inclusion in a clinical trial.

In certain embodiments, methods and compositions of the disclosure are used for drug response monitoring. For example, a phase 2 drug combo trial may be conducted. Patients are randomized to receive Drug 1 with or without Drug 2, or Drug 2 alone. Biopsies from patients are sequenced at the baseline and weeks later. Greater than 80% of proteases of interest are significantly changed in responders vs. non-responders (p=0.00036).

Figure 12:
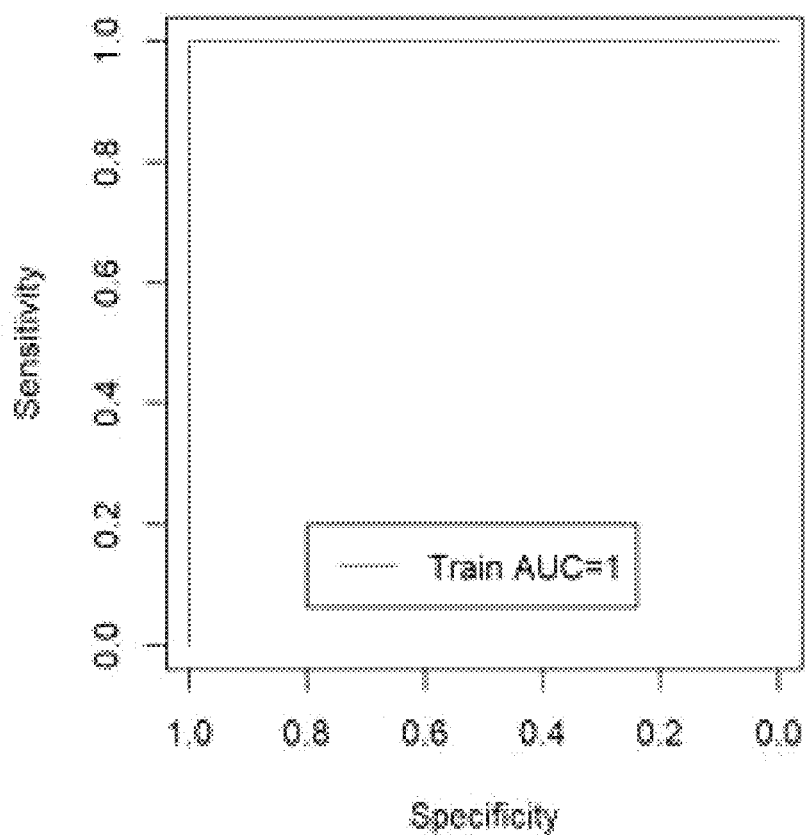
FIG. 12 shows response of responders vs. non-responders.

FIG. 12 shows the ROC curve for drug responders vs. non-responders. Significantly, in the depicted trial, the AUC is 1. The present invention may also be used for detection of conditions other than liver disease or liver cancer. Organ cancers with a high accumulation of the nanosensors according to the present invention are also considered.

Figure 13:
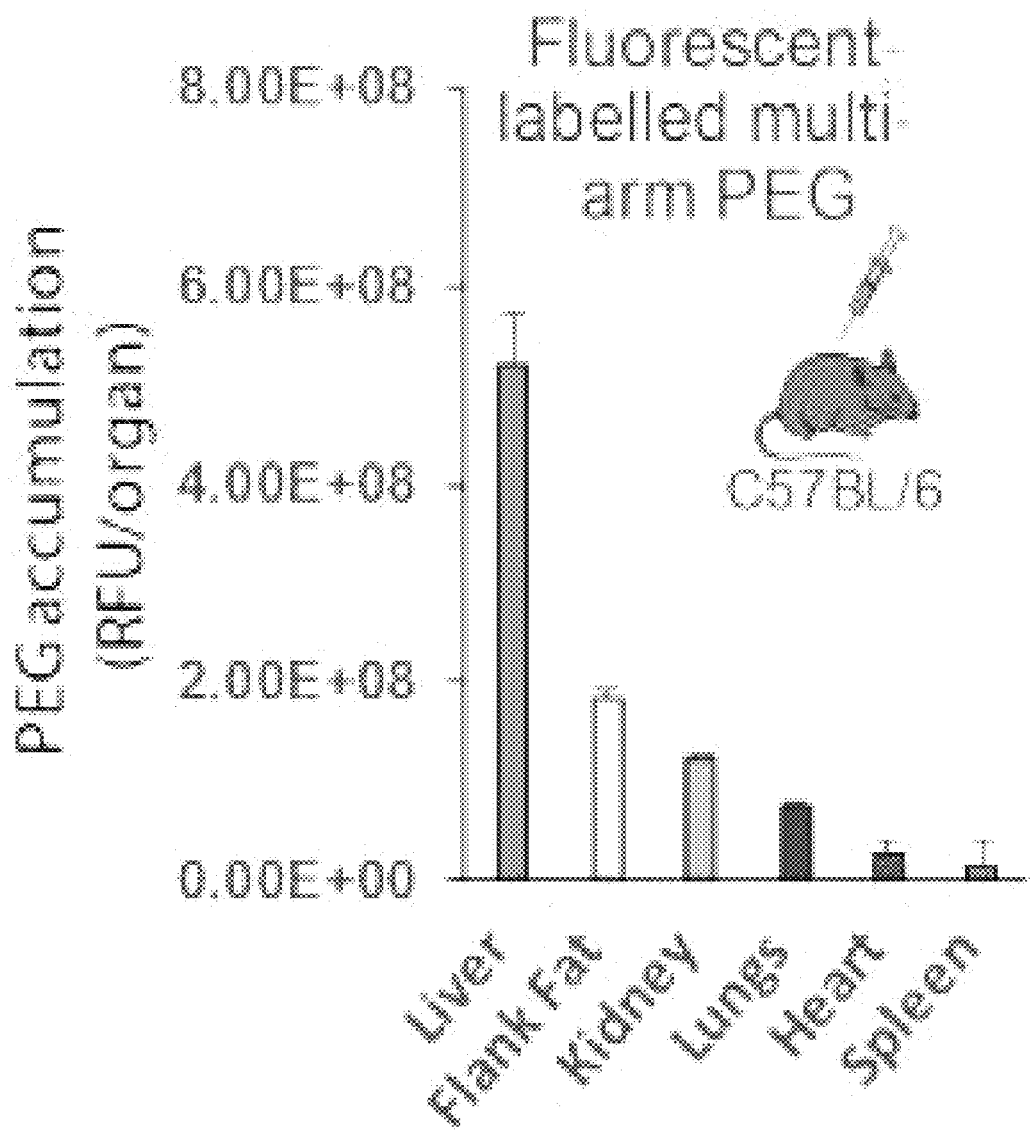
FIG. 13 shows organ accumulation of activity sensors.

FIG. 13 shows the PEG accumulation (RFU/organ) for C57BL/6 mice having organ cancers with a high accumulation of nanosensors according to the present invention. The bio-distribution of multi-arm PEG carrier is shown by the PEG accumulation (RFU) for liver, kidney, lungs, spleen, heart, and flank fat.

The present invention may be used for detection of liver conditions other than NASH, such as liver cancer or HCC. For example, protease signatures and nanosensors designed according to the present invention may be used to classify hepatocellular carcinoma (HCC). In the present invention, the activity sensors may be used to differentiate HCC from chronic liver disease (CLD). Analysis of TCGA human HCC database provide many samples for all stages of HCC, numerous for stage 1 of HCC, and numerous for non-tumor. 44 proteases are found to be shared among etiologies including HBV, HCV, ALD, and NAFLD. HCC-specific proteases are then identified. An area under the curve for training of the stage 1 HCC samples vs the non-tumor sample is 0.984. Validation produces an area under the curve of 0.948 for a stage 1 HCC sample vs a non-tumor sample. As such, the activity sensors may be used to characterize HCC and differentiate from other CLD with high sensitivity and specificity. The area under the curve increases in value when classifying HCC and differentiating from other cancer types (training AUC=1.0 for HCC sample vs. non-tumor or other tumor sample; validation AUC=0.999 for HCC sample vs. non-tumor or other tumor sample).

The present invention may achieve greater sensitivity and specificity than other available detection techniques. Other detection tests for HCC include ultrasound, computed tomography (CT), and magnetic resonance imaging (MRI). Liquid biopsy is also a potential testing method for detection. Ultrasound has an overall sensitivity of 94% and an early HCC sensitivity of 63%. CT has an overall sensitivity of 76% and an early HCC sensitivity of 58%. MRI has an overall sensitivity of 85% and an early HCC sensitivity of 67%. Wako Diagnostics supplies the AFP-L3, DCP biomarkers test which has an overall sensitivity of 83%. Glycotest supplies a Glycoprotein fucosylation test with an overall sensitivity of 93% and an early HCC sensitivity of 83-92%. Liquid biopsy may be used for HCC, but no sensitivity data is presently available. The methods are discussed in the following articles, which are incorporated herein: Singal et al. Aliment Pharmacol Ther 2009, 30:37-47; Nam et al. Clinical Gastroenterology and Hepatology 2011, 9:161-167; Hann et al., J Med Microb Diagn 2014, 3:1; Glycotest 2017 Investor Presentation; Mehta et al. Cancer Epidemiol Biomarkers Prev, 26(5) May 2017; Glycotest Press Release Jan. 4, 2018; and J. D. Cohen et al., Science 10.1126/science.aar3247 (2018).

Example 1

The activity sensors of the invention are designed to assess NASH disease severity and monitor treatment response. The activity sensors are used to evaluate associations between hepatic protease gene expression and fibrosis severity and to determine changes in protease expression according to fibrosis response.

For design of the activity sensors specific to NASH, RNA sequencing (RNAseq) is carried out to determine which proteases are expressed differentially in NASH. After determining which proteases are expressed in NASH, activity sensors are designed. In particular, reporters in the activity sensors are designed to be cleaved by the proteases differentially expressed in NASH liver tissue compared to healthy liver tissue.

Compositions of the invention are tested in mouse models for NASH. Human mRNA sequence (RNA-Seq) data are obtained from The Cancer Genome Atlas (TCGA) and used to identify protease targets for detection of NASH. Using a genetic mouse model of NASH, the expression of multiple target proteases is validated and a panel of protease-responsive activity sensors is designed. Upon administration, reporters are cleaved and detected in the urine of the mice using LC-MS/MS. Other aspects and advantages of the invention will be apparent upon consideration of the following detailed description thereof.

Specifically, RNAseq is performed on RNA extracted from procured formalin fixed and paraffin embedded (FFPE) liver tissue from between 50 and 200 patients with NASH and hepatic fibrosis as well as healthy controls. RNAseq is also performed on RNA extracted from fresh liver tissue obtained at baseline (BL) and weeks later (W) from subjects with NASH at various stages of fibrosis, treated with one or more therapeutics alone or in combination.

Next, the activity sensors are designed. Protease gene expression is compared between NASH patients and controls using statistical methods, and the associations between protease gene expression and fibrosis stage are evaluated, as well as evaluation of changes in gene expression according to fibrosis response (≥1-stage improvement), between BL and W. Results from analysis indicated that the expression levels of 9 protease genes, including FAP, ADAMTS2, MMP14, and MMP15, from multiple disease pathways including fibrosis, inflammation, and cell death are increased in NASH patients versus healthy controls (all P<0.05). The expression levels of 18 protease genes are positively correlated with fibrosis stage. Between BL and W, the expression of 7 proteases decreased (P<0.05) in patients with fibrosis response compared with non-responders. Compared to all genes, decreases in target proteases are enriched in fibrosis responders vs. non-responders.

Those results indicate that the hepatic protease expression in patients with NASH is correlated to fibrosis stage and treatment response. Thus, proteases involved in fibrosis, inflammation, and cell death are important in the progression of NASH.

One of skill in the art would know what peptide segments to include as protease cleave sites in an activity sensor of the disclosure. One can use an online tool or publication to identify cleave sites. For example, cleave sites are predicted in the online database PROSPER, described in Song, 2012, PROSPER: An integrated feature-based tool for predicting protease substrate cleavage sites, PLoSOne 7(11):e50300, incorporated by reference. Reproduced below is a set of exemplary protease substrates for a variety of significant protease. In the sequences shown below, the vertical bar shows the cleavage site, and forms no part of the sequence. Any of the compositions, structures, methods or activity sensors discussed herein may include, for example, any suitable cleavage targets including, for example, any of the sequences below as cleavage sites, as well as any further arbitrary polypeptide segment to obtain any desired molecular weight. To prevent off-target cleavage, one or any number of amino acids outside of the cleavage site may be in a mixture of the D and/or the L form in any quantity.

```
Aspartic protease HIV-1 retropepsin (A02.001)
A02.001:
                                      (SEQ ID NO: 1)
SSTS|SWYS

A02.001:
                                      (SEQ ID NO: 2)
PCIQ|AESE

A02.001:
                                      (SEQ ID NO: 3)
DDEE|IELA

A02.001:
                                      (SEQ ID NO: 4)
VLEQ|VVTS

A02.001:
                                      (SEQ ID NO: 5)
QVVQ|VVLD

Cysteine protease Cathepsin K (C01.036)
C01.036:
                                      (SEQ ID NO: 6)
KSIQ|EIQE

C01.036:
                                      (SEQ ID NO: 7)
KDFA|AEVV

C01.036:
                                      (SEQ ID NO: 8)
TSYA|GYIE

C01.036:
                                      (SEQ ID NO: 9)
LKVA|GQDG

C01.036:
                                      (SEQ ID NO: 10)
FCLH|GGLS

Calpain-1 (C02.001)
C02.001:
                                      (SEQ ID NO: 11)
WMDF|GRRS

C02.001:
                                      (SEQ ID NO: 12)
SATA|AVNP

C02.001:
                                      (SEQ ID NO: 13)
RELG|LGRH

Caspase-1 (C14.001)
C14.004:
                                      (SEQ ID NO: 14)
DEGD|SLDG

C14.004:
                                      (SEQ ID NO: 15)
DETD|MAKL

C14.004:
                                      (SEQ ID NO: 16)
EECD|AAEG

Caspase-3 (C14.003)
C14.003:
                                      (SEQ ID NO: 17)
AEVD|GDDD

C14.003:
                                      (SEQ ID NO: 18)
DRHD|GTSN

C14.003:
                                      (SEQ ID NO: 19)
VEVD|APKS
```

-continued

Caspase-7 (C14.004)
C14.004:
(SEQ ID NO: 20)
DQTD|GLGL

C14.004:
(SEQ ID NO: 21)
DSID|SFET

C14.004:
(SEQ ID NO: 22)
DDVD|TKKQ

Caspase-6 (C14.005)
C14.005:
(SEQ ID NO: 23)
VEMD|AAPG

C14.005:
(SEQ ID NO: 24)
VSWD|SGGS

C14.005:
(SEQ ID NO: 25)
EETD|GIAY

Caspase-8 (C14.009)
C14.003:
(SEQ ID NO: 26)
VETD|KATV

C14.003:
(SEQ ID NO: 27)
GSSD|PLIQ

C14.003:
(SEQ ID NO: 28)
DDAD|YKPK

Metalloprotease Matrix metallopeptidase-2 (M10.003)
M10.003:
(SEQ ID NO: 29)
HISS|LIKL

M10.003:
(SEQ ID NO: 30)
DPNN|LLND

M10.003:
(SEQ ID NO: 31)
DLSD|LTAA

M10.003:
(SEQ ID NO: 32)
FSAY|IKNS

M10.003:
(SEQ ID NO: 33)
EALP|LLVR

Matrix metallopeptidase-9 (M10.004)
M10.004:
(SEQ ID NO: 34)
QQGA|IGSP

M10.004:
(SEQ ID NO: 35)
GPPG|IVIG

M10.004:
(SEQ ID NO: 36)
MDIA|IHHP

M10.004:
(SEQ ID NO: 37)
FFKN|IVTP

M10.004:
(SEQ ID NO: 38)
GPLG|ARGI

-continued

Matrix metallopeptidase-3 (M10.005)
M10.005:
(SEQ ID NO: 39)
HLGG|AKQV

M10.005:
(SEQ ID NO: 40)
VWAA|EAIS

M10.005:
(SEQ ID NO: 41)
GPLG|ARGI

M10.005:
(SEQ ID NO: 42)
ESGD|YKAT

Matrix metallopeptidase-7 (M10.008)
M10.008:
(SEQ ID NO: 43)
VAQD|LNAP

M10.008:
(SEQ ID NO: 44)
SPDA|LQNP

M10.008:
(SEQ ID NO: 45)
PPLK|LMHS

M10.008:
(SEQ ID NO: 46)
GPHL|LVEA

Serine protease Chymotrypsin A (cattle-type) (S01.001)
S01.001:
(SEQ ID NO: 47)
VGPN|LHGV

S01.001:
(SEQ ID NO: 48)
GGGN|KIGP

Granzyme B (*Homo sapiens*-type) (S01.010)
S26.010:
(SEQ ID NO: 49)
LSTA|RFVV

S26.010:
(SEQ ID NO: 50)
VTED|VDIN

S26.010:
(SEQ ID NO: 51)
SALA|TTVY

Elastase-2 (S01.131)
S01.131:
(SEQ ID NO: 52)
QELI|SNAS

S01.131:
(SEQ ID NO: 53)
QELI|SNAS

S01.131:
(SEQ ID NO: 54)
WELI|SNAS

Cathepsin G (S01.133)
S01.133:
(SEQ ID NO: 55)
SGNY|ATVI

S01.133:
(SEQ ID NO: 56)
SIQM|NVAE

S01.133:

QQNY|QNSE (SEQ ID NO: 57)

Thrombin (S01.217)
S01.217:
SILR|LAKA (SEQ ID NO: 58)

S01.217:
KFQR|AITG (SEQ ID NO: 59)

S01.217:
AEPK|MHKT (SEQ ID NO: 60)

S01.217:
TIPR|AAIN (SEQ ID NO: 61)

Plasmin (S01.233)
S01.233:
AEFR|HDSG (SEQ ID NO: 62)

S01.233:
RRKR|IVGG (SEQ ID NO: 63)

S01.233:
AMSR|MSLS (SEQ ID NO: 64)

Glutamyl peptidase I (S01.269)
S01.269:
PEPE|QLKM (SEQ ID NO: 65)

S01.269:
QSKE|AIHS (SEQ ID NO: 66)

S01.269:
KLKE|ASRS (SEQ ID NO: 67)

Furin (S08.071)
S08.071:
RAKR|SPKH (SEQ ID NO: 68)

S08.071:
RKKR|STSA (SEQ ID NO: 69)

Signal peptidase I (S26.001)
S26.001:
SAMA|ADSN (SEQ ID NO: 70)

S26.001:
TLLA|NINE (SEQ ID NO: 71)

Thylakoidal processing peptidase (S26.008)
S01.269:
QAEE|TYEN (SEQ ID NO: 72)

S01.269:
DVID|MSKE (SEQ ID NO: 73)

Signalase (animal) 21 KDa component (S26.010)
S26.010:
EVLA|TPPA (SEQ ID NO: 74)

S26.010:
APVP|GTAW (SEQ ID NO: 75)

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

---

What is claimed is:

1. A method for characterizing liver disease, the method comprising:
   detecting, in a sample from a subject, a quantity of each of a plurality of distinct reporters that are released from activity sensors, wherein different members of the plurality of reporters are released by proteases that are differentially active in diseased liver tissue versus healthy liver tissue, the proteases comprising at least 4 different proteases selected from the group consisting of FAP, MMP2, ADAMTS2, FURIN, MMP14, GZMB, PRSS8, MMP8, ADAM 12, CTSS, CTSA, CTSZ, CASP1, ADAMTS12, CTSD, CTSW, MMP11, MMP12, GZMA, MMP23B, MMP7, ST14, MMP9, MMP15, ADAMDEC1, ADAMTS1, GZMK, KLK11, MMP19, PAPPA, CTSE, PCSK5, and PLAU;
   determining and classifying that the subject has nonalcoholic steatohepatitis (NASH) at one of stages NASH F1, NASH F2, NASH F3, or NASH F4, based upon relative quantities of the detected reporters, thereby characterizing the disease.

2. The method of claim 1, wherein the quantities of the detected reporters are collected from a urine sample obtained from the subject to whom the activity sensors was administered.

3. The method of claim 1, further comprising measuring quantities of the plurality of detected reporters.

4. The method of claim 3, further comprising correlating quantities of the plurality of detected reporters to a rate of progression or regression of the liver disease.

5. The method of claim 1, wherein the proteases include at least one of a serine protease, a cysteine protease, a threonine protease, an aspartic protease, and a metalloprotease.

6. The method of claim 5, wherein the reporters are released via enzymatic cleavage.

7. The method of claim 1, wherein at least 10 different proteases are selected.

8. The method of claim 1, wherein the activity sensor comprises a multi-arm polyethylene glycol (PEG) scaffold and the reporters comprise polypeptides linked to the PEG scaffold.

9. The method of claim 1, wherein relative quantities of detected reporters released by the selected proteases determines the stage of NASH with a sensitivity and specificity comprising an area under the curve (AUC) value of 0.98.

* * * * *